US008137959B2

(12) United States Patent
Castillo Fernandez

(10) Patent No.: US 8,137,959 B2
(45) Date of Patent: Mar. 20, 2012

(54) METHOD OF CELL CULTURES AND DEVICE FOR IMPLEMENTING IT

(75) Inventor: Jose Antonio Castillo Fernandez, Brussels (BE)

(73) Assignee: Artelis S.A., Brussels (BE)

(*) Notice: Subject to any disclaimer, the term of this patent is extended or adjusted under 35 U.S.C. 154(b) by 912 days.

(21) Appl. No.: 12/098,202

(22) Filed: Apr. 4, 2008

(65) Prior Publication Data

US 2008/0248552 A1    Oct. 9, 2008

Related U.S. Application Data

(63) Continuation-in-part of application No. PCT/EP2006/066981, filed on Oct. 3, 2006.

(30) Foreign Application Priority Data

Oct. 4, 2005    (BE) .................................. 2005/0483

(51) Int. Cl.
*C12M 1/12*    (2006.01)
*C12M 1/00*    (2006.01)
*C12M 3/00*    (2006.01)

(52) U.S. Cl. ............... 435/297.2; 435/289.1; 435/297.1; 435/304.1; 435/296.1; 435/818; 435/295.1; 435/295.2; 435/295.3

(58) Field of Classification Search .............. 435/295.1, 435/295.2, 295.3, 289.1, 297.1, 297.2, 304.1, 435/296.1, 818
See application file for complete search history.

(56) References Cited

U.S. PATENT DOCUMENTS

| 2,083,348 | A | * | 6/1937 | Scholler et al. ............ 435/295.2 |
| 4,978,616 | A |   | 12/1990 | Dean, Jr. et al. |
| 5,501,971 | A |   | 3/1996 | Freedman et al. |
| 6,864,084 | B2 | * | 3/2005 | Schob ........................ 435/293.1 |
| 7,320,889 | B2 | * | 1/2008 | Kahlert et al. ............. 435/295.3 |

FOREIGN PATENT DOCUMENTS

| DE | 38 18 776 A1 | 12/1989 |
| JP | 08-070844 | 3/1996 |
| JP | H08506019 | 7/1996 |
| JP | 2000069954 | 3/2000 |
| JP | 2002085049 | 3/2002 |

OTHER PUBLICATIONS

English translation of DE 3818776 A1.*
International Search Report (PCT/EP2006/066981) mailed Feb. 2, 2007.
Written Opinion of the International Searching Authority (PCT/EP2006/066981) mailed Feb. 2, 2007.
International Preliminary Report on Patentability (PCT/EP2006/066981) issued Apr. 8, 2008.
Examination Report Established by Australian Patent Office for Singapore Patent Application No. SG 200802471-3, mailed Jun. 17, 2009.
Search Report Established by Australian Patent Office for Singapore Patent Application No. SG 200802471-3, mailed Jun. 17, 2009.

* cited by examiner

*Primary Examiner* — Nathan Bowers
(74) *Attorney, Agent, or Firm* — King & Schickli, PLLC

(57) ABSTRACT

The invention generally provides a cell culture vessel having at least one first zone and at least one second zone, wherein the first zone is a transfer zone for a culture medium which essentially contains no cells and the second zone is a cell culture zone. The invention further includes methods utilizing the cell culture vessel.

32 Claims, 9 Drawing Sheets

METHOD OF CELL CULTURES AND DEVICE FOR IMPLEMENTING IT

CROSS-REFERENCE TO RELATED APPLICATIONS

This application is a continuation-in-part of International Application No. PCT/EP2006/066981, filed Oct. 3, 2006, which in turn, claims the benefit of Belgian patent application No. 2005/0483, filed Oct. 4, 2005. The disclosures of each of the aforementioned applications are incorporated herein by reference.

FIELD OF THE INVENTION

The present invention relates to culture of cells by means of a device comprising:

a culture vessel provided with a cover, in which there is situated at least one first zone and at least one second zone, said first zone being a transfer zone for the culture medium essentially free from cells and said second zone being a cell culture zone, means of circulating the culture medium, allowing circulation of the culture medium through the culture zone, said culture zone comprising a bottom wall and a top wall, each wall being provided with orifices allowing a transfer of culture medium essentially free from cells.

BACKGROUND OF THE INVENTION

Culture devices are known for example from the U.S. Pat. No. 5,501,971 which describes a culture vessel in which there is situated a culture zone external to an internal medium transfer conduit. The cells are situated in the external culture zone, which is a sort of basket comprising carriers, and the culture medium flows from top to bottom through this culture zone. Next the medium is recovered in the bottom part of the culture zone, it is taken up by means of a medium circulation device through the above mentioned conduit into a top part of the culture vessel and then passes again through the culture zone. The U.S. Pat. No. 5,507,971 describes several alternatives, but the medium always passes through the culture zone from top to bottom.

One drawback of such a device is that it is not adapted to all types of cell culture. Indeed this device is solely designed for cell culture on microcarriers in a fixed or close-packed bed, and is absolutely not suitable for cell culture in suspension or on microcarriers in a fluidised bed. Indeed, in the device of the U.S. Pat. No. 5,501,971, the cells in suspension without carriers or microcarriers or on non-immobilised carriers have a tendency to sediment and to accumulate in the bottom of the culture zone since they are subject to gravity and, as the flow of medium through this culture zone takes place from top to bottom, this accumulation of cells in the bottom of the culture zone is all the greater. Consequently the cells are packed on top of one another and are in contact with each other and the nutriments in this zone are not very accessible for the cells.

In the reactor of the U.S. Pat. No. 5,501,971, in the case of cultures, on non-immobilised carriers or microcarriers, of cells which are fragile species withstanding few stresses, the cells are subjected to the effect of gravity, to the descending flow of the medium and to the weight of the carriers, which enormously impairs the survival of the culture. In addition, an application for the culture in suspension is inconceivable in the bioreactor of the U.S. Pat. No. 5,501,971 since the cells in suspension can under no circumstances be subjected to cell to cell contact. Indeed, if such contacts are present, the cells create protein bonds between them and aggregate. Such aggregation creates cell death through lack of oxygen and nutriment.

U.S. Pat. No. 5,270,207, discloses a device wherein culture medium flows from the bottom to the top through the culture zone. The space inbetween the culture zone and the outer side wall of the device is filled with medium flowing upwards. The medium undergoes gas exchange in the upper space of the device whereafter it flows downwards again via a cylindrical zone in the center of the device towards the bottom of the device. In such devices, only a limited amount of gas exchange can take place, which makes these less suitable for cell culturing method wherein extensive cell growth or metabolism takes place.

SUMMARY OF THE INVENTION

The aim of the invention is to mitigate the drawbacks of the prior art by procuring a culture device making it possible to cultivate both cells in suspension and anchorage-dependent cells on carriers or microcarriers whilst ensuring minimum stress on the cells and preventing this accumulation of cells in the bottom of the culture zone.

To solve this problem, a device as indicated at the beginning of this text, is provided according to the invention, characterised in its broadest sense in that it also comprises at least one third and at least one fourth zone, both being culture medium transfer zones essentially free from cells, said third zone being in medium communication with the first and second zone and said fourth zone being in medium communication with the second zone (the culture zone) and with the first zone (the medium transfer zone) via the culture medium circulation means, and in that the culture medium circulation means allow a circulation of the culture medium from bottom to top in said second culture zone.

More particularly said third zone (4), has an overflow (37) so that the culture medium overflows from the first culture medium transfer zone (3) to the third culture medium transfer zone (4).

According to a more particular embodiment the third zone is a zone internal to said second zone and external to said first zone and said fourth zone is a zone external to said second zone According to an alternative embodiment the third zone is a zone located entirely below the second zone and entirely above the first zone.

According to a particular embodiment a device according to the invention comprises flow redistributing elements in the third zone or closed regions in the bottom wall of the second zone for providing a homogenous flow of medium into said second zone.

Said fourth zone more particularly encloses a volume of gas consisting of the ambient atmosphere of the bioreactor and can also constitute an oxygenation zone for this culture medium.

Consequently, the medium which passes through the first medium transfer zone from bottom to top reaches the top of the first medium transfer zone and overflows into the third zone, which is in medium communication with the first zone, the medium flows downwards, subjected to the flow imposed by the circulation means, to gravity and to the communicating vessels effect, passes through medium-passage orifices in the bottom wall of the second culture zone, next travels up again towards the top of the culture zone by a communicating vessels effect or by an effect due to the medium circulation means, or by both, and then overflows into the fourth medium transfer zone, which is in communication with the first medium transfer zone via the circulation means. The medium circulation means then once again take the medium to the top of the first medium transfer zone and the cycle recommences. Consequently, the cells which are situated in the culture zone traveled through from bottom to top by the culture medium benefit from a gravity effect partly counteracted by the flow of medium. The flow allows better dispersion of cells alone or on microcarriers in the culture zone and the harmful stresses for them are reduced.

When the terms cells on carriers or on microcarriers are used, it must be understood that the carriers can be in a fixed or packed bed or in a fluidised bed.

Likewise, when the terms "cell culture" or "cells" are used, it must be understood in particular that animal cells are being referred to, whether it be for viral production, proteins or other recombinant products, cellular metabolites, a culture of tissue cells (possibly on three dimensional carriers), stem cells or bacteria or yeasts.

It will be easily understood by the skilled in the art that cells on carriers or microcarriers suffer less from packing, in particular in the case of a fixed bed, than cells in suspension without carriers or without microcarriers, but nevertheless he will easily see the advantage in the oxygenation of the culture and in the nutrition thereof of such a flow direction within the culture zone. Indeed it is well known that the design of culture vessels is a key step in cell culture. The design of these must be such that there are no dead areas, not supplied with fresh medium, or in which the cells would accumulate; it is also very advantageous for the cells to be in direct contact with the culture medium rather than with one another for their reproduction and/or production metabolism.

Hence the invention provides a flexible device adapted to suspension cultures and cultures on carriers or on microcarriers which allows a reduction in the stresses applied to the cells and which prevents the accumulation of cells in a particular zone of the culture zone, by reducing the effect of gravity which is exerted on the cells and preventing the presence of dead zones not supplied with fresh medium or in which the cells can accumulate. In addition, for application in suspension culture, devices according to the invention allows a good dispersion of cells by virtue of on one hand the upward flow and on the other hand the gravity which is still partly applied to the cells.

The terms "bottom wall provided with orifices for the passage of a medium essentially free from cells" must be taken to mean a wall situated in the bottom part of the culture zone, which may be situated at the bottom of the culture zone or in the lower part of a vertical wall delimiting said culture zone and which allows the culture medium to pass and not the cells on microcarriers or carriers or even in suspension. Similarly, the top wall provided with orifices for the passage of a medium essentially free from cells may be a wall situated at the top of the culture zone or at a top part of the vertical wall delimiting the culture zone with characteristics identical to those described above.

Naturally the medium which overflows from the first zone into the third zone can overflow over the top of the walls of the first zone and in this way reach the third zone or can overflow via an orifice or tube installed in the top or bottom part of the first medium transfer zone. The same applies to the medium which overflows from the second zone into the fourth zone.

Advantageously, the culture medium circulation means consist of a centrifugal pump situated in a bottom part of said culture device, comprising at least one magnetic device rotating about a substantially central rotation axis (real or virtual), at least one inlet and at least one outlet for the culture medium, said circulation means being provided for sucking the medium in a siphon created by a rotation of the magnetic device and for propelling the medium towards the culture medium discharge placed in a zone external to said magnetic device and in that said centrifugal pump is driven by a rotary magnetic motor provided for effecting a circulation of medium with no communication with the outside of the device, and at least one guidance device, designed to guide the culture medium propelled through said outlet towards the top of the vessel.

One drawback of the existing conventional bioreactor is that they are provided with a blade or screw agitation system for providing homogenisation of the culture medium within the culture vessel without necessarily providing adequate circulation. In this case, the bioreactor comprises a spindle provided with double fragile mechanical linings, for example made from expensive silicon carbide and which passes through the cover of the bioreactor. This passage through the cover of the bioreactor is a serious risk of contamination and a significant risk of breakdown.

Other types of bioreactor comprise an external circulation of the culture medium. The medium passes through a pipe through a peristaltic pump or a similar system. Obviously, this solution, although partly preventing direct contaminations, has another drawback. It is not applicable for long-life cultures. Indeed, the pipes used in this type of pump are subject to wear during long life cultures, which also involves problems of sealing and contamination.

The medium circulation as described above also gives rise to a technical difficulty of achieving a "fountain" effect. It therefore does not suffice to make the liquid flow through the culture zone at a very low pressure drop, it is also necessary to maintain a difference in level inside the culture vessel simultaneously. Indeed, bringing the liquid towards the top of the first medium transfer zone is a key step, but also ensuring that the medium does not accumulate excessively in the bottom of the fourth zone too. If the culture medium accumulates in the bottom of the fourth culture zone, the overflow effect will be reduced and the cyclic circulation of the medium from the first medium transfer zone to the third medium transfer zone and then to the second culture zone and finally into the fourth medium transfer zone will not be optimum.

Consequently, the circulation means according to the invention will comprise a magnetic device rotating about a substantially central rotation axis, and a culture medium inlet and outlet.

For small-scale cultures, the magnetic device will for example be a simple magnetic bar, driven by an external magnet, affording flow rates of 0.6 to 6 l/min (that is to say 1 to 10 ml/sec). Because of this, there is no risk of contamination since the medium circulation system does not communicate with the outside but is driven by a device external to the culture vessel. A peristaltic pump can also be envisaged according to the invention, but preferentially for short duration cultures.

For cultures on a larger scale, the magnetic device will be a magnetised rotor with a flow rate of between for example 10 and 200 l/min, in particular 20 to 150 l/min and preferably 25 to 100 l/min.

In a particular embodiment, a device according to the invention comprises a series of modules, each module comprising said first zone, said second zone, said third zone and said fourth zone, and in which the adjacent modules in said series of modules are in medium communication, said first zone and said fourth zone of each module being in communication with said circulation means, directly or indirectly.

This embodiment makes it possible to obtain a particularly flexible device and allows an increase in scale up to a volume of 100 liters.

Generally, the scaling up is a complex step in the production of recombinant products, viruses, cell metabolites or others or in the culture of cells since this scaling up generally gives rise to problems with zones supplied in a mediocre manner, whether it be with oxygen or with nutriments. In the embodiment described above, the culture device comprises a series of adjacent modules, for example stacked or juxtaposed. From the fourth zone of the first culture module, the culture medium reaches the medium circulation means by passing through the other culture modules. The invention envisages various types of module of predetermined volume. For example, modules of 500 ml or 5 liters, having a volume from 500 ml to 5 liters, including all volumes comprised within the range or framing the range. Consequently, for a culture of 3 liters, 6 modules of 500 ml will be used. For example, six modules will be stacked either in a sufficiently large vessel or by means of modules that can be interconnected so as to form said vessel.

In the case of the reactor of the document U.S. Pat. No. 5,501,971, if a culture volume of 3 liters is required, a culture zone height H would be needed. The medium which reaches the bottom of the culture zone in this patent is practically exhausted, in particular with regard to oxygen. Moreover, the authors of the U.S. Pat. No. 5,501,971 contemplate placing a oxygen sensor at the top of the culture zone and at the bottom of the latter and oversupplies the environment of the reactor with oxygen. Unfortunately, this type of over-oxygenation is absolutely not to be recommended since this produces an oxidation of cellular components of the cells at the top of the culture zone and cell death follows. In addition, when the authors of the U.S. Pat. No. 5,501,971 contemplate a scaling up, it is in terms of width that this is carried out since in terms of height it is no longer possible. Naturally, the space occupied on the floor quickly becomes uncontrollable. As it is known for the skilled in the art, floor space is a critical parameter, especially in white rooms where efficiencies are calculated according to the volume of air to be treated in order to obtain sterile air, this type of air treatment being very expensive. The volume of air to be treated is obtained by multiplying by the height of the "white room" the surface on the floor occupied by the bioreactor, its equipment, and persons handling the culture device.

Consequently, through the use of stacked or juxtaposed modules, according to yields to be achieved, the floor space is reduced. In addition, the volume of culture through which the culture medium must percolate before once again being in contact with the ambient air of the bioreactor is appreciably reduced. In the case of our previous example, the volume is divided by 6.

According to one advantageous embodiment, provision is therefore also made to design an autoclavable, empty, culture vessel with a predetermined height (made from glass or stainless steel) or an empty disposable culture vessel, comprising the medium circulation means in the bottom of the vessel. It will then suffice to position the number N of modules required in the vessel above the medium circulation means and to close the vessel again by means of an adapted cover. In this case, whether for a culture of 5 liters or 50 liters, the size of the vessel remains the same.

This embodiment can be particularly advantageous for laboratories having few means since it is particularly inexpensive. Indeed, if the vessel supplied is designed for a culture of 35 liters and a culture of only 5 liters or 10 liters is required, it suffices to place, for example above the culture medium circulation means, one or two culture modules of 5 liters. This particularly reduces the amount of investment since the expensive part always remains the same for any culture from 5 to 35 liters.

In addition, whether for a culture of 5 liters or 35 liters or even more, the floor surface will be the same, and the scaling up does not involve any greater volume of air to be treated. In addition, through the fact that the medium is, between each passage in a module, in contact with the ambient air in the reactor, the problems of scaling up are greatly reduced.

As mentioned previously, the medium circulation means are particularly effective by covering ranges of values particularly adapted to devices according to the invention. Consequently, the flow rate in each module is identical and, at the level that is output, the increase in scale is also not a problem according to the invention.

In a particularly advantageous embodiment, the circulation means are confined in a base module, said base module being in medium communication with at least one first medium transfer zone and at least one fourth medium transfer zone, directly or indirectly.

Since the medium circulation means are often zones presenting risk of cross contamination or external contamination through the presence of some not accessible zones for cleaning, procuring a base module which can for example, without however being limited thereto, be inserted in a simple glass vessel is particularly advantageous. This base module is adapted to the culture modules, allowing the communication of medium between the first medium transfer area of all the modules present and the medium outlet of the medium circulation means and allowing medium communication between all the fourth zones of all the culture modules present and the inlet of culture medium into the medium circulation means, directly or indirectly, that is to say passing through another module or not.

Devices preferably also comprises a head module, said head module comprising at least the cover. This head module being able to be designed to close off the superimposition mentioned above.

In an advantageous embodiment, at least one fourth zone comprises at least one substantially vertical or inclined flow wall.

The presence of this flow wall reduces the formation of foam which could appear during the overflow from the second culture zone to the fourth medium transfer zone. Indeed, without this flow wall, the flow of medium from the second to the fourth zone would be a turbulent flow, which would necessarily have as its consequence an undesirable formation of foam. It should be stated that the formation of foam is a major problem in many culture methods since the culture medium is rich in proteins. Stirring a fluid rich in protein always causes the appearance of foam. Consequently a turbulent flow would have this same consequence, and this is why, advantageously, the invention comprises said flow wall for reducing the flow turbulence.

In addition, this fourth medium transfer zone is also a zone in which the medium is in contact with the ambient atmosphere of devices according to the invention. The presence of the flow wall improves this contact and therefore the exchanges of oxygen between the ambient atmosphere and the culture medium, by increasing the gas-liquid contact surface area.

Advantageously, in order to stabilise the film, it is also possible to add additives to the culture medium in order to modify the rheological properties of the water such as the additives included in the group consisting of surfactants, Pluronic F68, glycerine, quaternary ammoniums and any other additive for modifying the rheological properties of the culture medium.

In a particularly preferred embodiment, the essentially vertical or inclined flow wall comprises a hydrophilic membrane.

Indeed, if the flow wall is not or does not comprise a hydrophilic surface, it may be very difficult to obtain a film of medium on this surface. In addition, the film, when it is formed on a conventional wall, is unstable. Consequently, by covering the flow wall with the hydrophilic membrane which fulfils the role of a sponge, the medium is naturally spread and flows evenly. Consequently, the contact surface between the film of medium and the ambient atmosphere is greatly improved, which permits oxygenation compatible with high cell densities. The coefficients of total transfer of oxygen obtained are from about $10^{-3}$ to about $10^{-2}$ $s^{-1}$.

If, in the embodiment with culture modules, some or all of the fourth zones comprise a flow wall with a hydrophilic membrane, the gas-liquid to exchanges are further improved. Consequently, even the last module in the series is supplied with an oxygenated medium. In some cases of the prior art with circulation of medium, when a culture is produced, for example with a volume of 200 liters, the cells at the end of the medium circulation are relatively undersupplied and the cell growth is not homogenous in the bioreactor.

In devices according to the invention, this is not the case; no undersupplied or dead zone exists.

In one advantageous embodiment, devices according to the invention comprise at least one gas inlet orifice and one gas outlet orifice.

The culture vessel preferably comprises at least one gas inlet orifice and one gas outlet orifice. In this way, it is possible to enrich the ambient atmosphere of devices according to the invention with oxygen for example, as the oxygen is consumed by the cells. It is also possible to supply the ambient atmosphere with other gases, for example by adding CO2 in order to modify the pH, or any other gas generally used in cell culture. The outlet orifice making it possible to prevent overpressures and to discharge the gas with a low oxygen content or simply part of the gas of the ambient atmosphere in order to reduce the ambient pressure of a device according to the invention. Also, provision is made to be able to close off or "strangle" this gas outlet in the case where a slight overpressure is desirable.

The gas inlet can be situated or connected to the first, to the second, to the third or to the fourth zone of the culture vessel. The first and fourth being preferential zones. The third medium transfer zone is not very accessible for gas-liquid contacts and the second zone of the culture vessel is the cell culture vessel, in which direct gas-liquid contact could present a risk of oxidation of the cell components, which is not desirable.

Advantageously, the gas inlet orifice is connected to at least one fourth medium transfer zone.

Because the fourth medium transfer zone also serves as an oxygenation zone since it is in the latter that the gas-liquid contacts are the greatest, with or without a flow wall, it is advantageous for it to be the latter that directly receives the addition of fresh gas in order to promote the oxygenation of the medium. In addition, the culture medium which overflows into this fourth zone is the medium used up by the cells, and therefore part of the oxygen is consumed, it may also need a modification to the pH and it is therefore an advantage for the gas (oxygen, air, $CO_2$ or other) to enter through this fourth culture zone in order to increase the efficiency of any regulation or oxygenation or modification of pH.

In a particular embodiment, the gas inlet is connected to a sparger tube.

The invention, in a particular embodiment, provides for a dispersion of gaseous bubbles to be effected within a device according to the invention. The dispersion of bubbles can be effected by a sparger immersed in the culture medium in the first, second, third and fourth medium transfer zone (large bubbles or microbubbles, according to the application). The dispersion of bubbles will preferably be effected by a sparger immersed in the culture medium in the first or fourth medium transfer zone.

In a particular embodiment, the cover of the culture vessel is connected to at least part of said top wall of at least one second culture zone.

This particularly preferred embodiment allows a simplified taking of samples which minimises the risks of contamination. Particularly during cultures on microcarriers, taking samples is not generally a step without any risk. To measure the cell density, at the present time there exist only a few means, which are also not very reliable and tedious. Consequently the best means of measuring the cell density is sampling carriers and observing them under the microscope, possibly after colouring.

Indeed, in conventional bioreactors, and in particular in the bioreactor of the U.S. Pat. No. 5,501,971, taking samples is either impossible because the top wall of the culture zone cannot be opened simply or it represents a serious risk of contamination. Indeed, the user should open the cover of the culture vessel, which is often bulky and heavy and therefore difficult to move in a sterile flow, and then hold the cover, generally fixed to a blade or other device for raising the medium and therefore heavy and bulky, and he should ensure that he does not touch anything and hold it in one hand in order not to contaminate it. Next, with the other hand, he must open the top wall of the culture zone and hold it in the other hand. Then, by means of a clamp in a third hand, he must sample one or more carriers in order to be able to evaluate the cell density. This requires the presence of a second user or impressive dexterity.

The invention greatly simplifies this step of taking samples by procuring a cover fixed to the top wall of the culture zone; all that needs to be done then is to slightly lift the cover, the top wall of the culture zone rising simultaneously, and to introduce a sterile clamp or a sampling tool such as a pipette or the like for sampling one or more carriers in order to evaluate the cell density. The risks of touching a non-sterile object and the risks of contamination are greatly reduced.

Advantageously, in certain embodiments, devices according to the invention also comprise a heating means, designed to heat the transferred culture medium. This heating means can advantageously be situated in the fourth medium transfer area or at the medium circulation means. Naturally, the first zone can also comprise this heating means.

The heating means can be an electrical element, an electrical coil or any other heating means generally used in the field of cell culture, such as for example a thermostatically controlled double jacket.

Indeed, during large or very large scale culture, it is not always easy to place a device according to the invention in a thermostatically controlled device or room. Consequently the invention solves this problem by directly placing heating means in order to control the culture medium thermostatically and to afford an even temperature throughout the culture vessel. Preferably, a device according to the invention provides a heating of the medium without any overheating point.

In certain embodiments, devices according to the invention comprises sensors for measuring culture parameters, said sensors being in contact with the culture medium. Culture parameters means, amongst other things, the dissolved oxygen partial pressure, the pH, the temperature, the optical density, certain concentrations of nutriments, such as lactate, ammonium, carbonates, glucose or any metabolic product or product to be metabolised which could for example reflect the cell density.

It can also be contemplated according to the invention using regulation loops according to these parameters. These regulation loops would for example modulate the quantity of oxygen to be injected into the gaseous atmosphere according to the value of the dissolved oxygen partial pressure present or the quantity of dissolved oxygen consumed by the cells. It could inject $CO_2$ according to the pH value obtained by the sensors or any other type of regulation generally used in this type of culture.

The sensors are preferably arranged in a bottom part of at least one fourth zone. The fourth medium transfer zone is a preferential zone for the positioning of the sensors since the values obtained by the latter are clearly representative of the cell consumption since this zone has the medium coming from the culture zone passing through it.

Advantageously, said sensors are disposable optical sensors, provided for transmitting an optical signal representing the parameters to be measured through said culture vessel to an optical signal receiver, external to said device.

In a particularly preferential embodiment, the device comprises a series of modules, each culture module comprises in its top part a first fixing means and in its bottom part a second fixing means, in which said base module also comprises in a top part a first fixing means and said head module also comprises in its bottom part a second fixing means, said first fixing means and said second fixing means being complementary fixing means for producing a stacking sequence from the bottom to the top of a base module, at least one culture module and a head module.

Advantageously, said first and said second fixing means comprise means for producing said stacking sequence in a gas- and liquid tight manner.

Indeed, according to the invention, it is possible to design a series of modules where the wall of each module would constitute part of the wall of the culture vessel. Next, it suffices to assemble this series of culture modules with a base module comprising the circulation means and a head module comprising the cover. The assembly formed by these modules would then constitute the culture device. According to the culture volume necessary, a number N of modules would be fitted together to construct one's own culture device with a height H.

In a very particular embodiment, devices according to the invention is a disposable device.

There exist at the present time a quantity of bioreactors which give excellent cell culture results on a small and large scale. Unfortunately, these bioreactors are expensive in terms of cleaning, sterilisation, labour, location and space occupied. Indeed, in particular for the production of clinical batches or products of pharmaceutical interest, it is essential for the bioreactors to be placed in sterile white rooms. A 500 liter bioreactor occupies more than twenty times its volume in a white room. The white room criterion is the volume used by an installation, that is to say, if the installation occupies 1 $m_2$ of floor surface, the volume of the air to be treated will be (1 $m_2$ plus the surface area necessary for the user) multiplied by the height of the white room since the volume of air above the floor surface is also to be treated. In addition, the sterilisation, aseplicisation, washing, sanitisation, etc protocols, which are steps required both for a bioreactor and for the room occupied, are extensive and tedious protocols which impose enormous costs both with regard to labour and installation of products. This is why, principally in pharmaceutical, biological and biochemical laboratories and in white rooms, disposable equipment, generally less bulky, not requiring cleaning, sanitisation, sterilisation and asepticisation, is being increasingly used each day.

Alternative solutions to reusable conventional bioreactors exist, for example culture is known in a disposable sterile container which is stirred by a stirring plate reproducing a wave movement, for example the WAVE® bioreactor. Unfortunately, such a bioreactor presents a problem of scaling up since a 500 liter container, in so far as the stirring plate can be sized, has an enormous floor surface which has a white room air treatment cost that it is impossible to assume, without mentioning the difficulty of handling such containers, taking samples and placing culture parameters sensors.

Other solutions exist, such as stirred disposable flasks called "spinners". The scaling up of these flasks is also impossible and the flasks have a low oxygen transfer as well as stresses on the cells during stirring.

There also exists culture in a CELLCUBE® or CELLFACTORY® system. Such a system is difficult to regulate and is bulky. In addition, the oxygen transfers are poor and it requires incubators of large size. Once again, scaling up is tedious.

The BELLOCELL® system is also known. This system is based on immobilising cells in porous matrices, which are packed in a culture zone. The medium is in a lower zone provided with a compressible bellows. The medium rises and falls alternately in order to immerse the matrices in the medium and then expose them to the ambient air.

Unfortunately, the scaling up of this system is also difficult. It is difficult to regulate and measure the culture parameters. In addition, the cells undergo tension stresses on their surface, being exposed first of all to a falling medium edge, drying, and then a rising medium edge, which is detrimental to their growth.

In summary, there exists at the present time no disposable cell culture system adapted for culture on a large and small scale which is easy to use, both in a white room and in the laboratory.

The invention therefore procures a very innovative solution which solves a major part of these drawbacks by procuring an unexpected system, applicable on a small and large scale, suitable for culture in suspension, on carriers or on microcarriers, the stirring of which affords homogeneity of the culture medium without dead zones nor cell accumulation zones. In addition, the risks of contamination because of the absence of a central spindle are particularly low, or even non-existing.

In fact, devices according to the invention present all the advantages of conventional bioreactors, as mentioned here previously, whilst being disposable. Devices according to the invention is stirred magnetically by medium circulation means based on a centrifugal pump, which do not have any contact with the outside. Heating means, for example an electrical coil, also afford homogeneous heating of the medium without having contact with the outside.

In addition, as mentioned above, in a particularly preferential manner, the culture device according to the invention comprises sensors which are disposable optical sensors, designed to transmit an optical signal representing the parameter to be measured through said culture vessel to an optical signal receiver, external to said device.

Consequently, the culture parameters are also measured through a wall of the device and this does not involve any contact with the outside, unlike the dissolved oxygen or pH probes passing through the cover of classical bioreactors, presenting a risk of poor cleaning in these probe passage orifices and of contamination through lack of a seal.

The sensors can be situated in the bottom part of the device or in the top part or both. When the sensors are present in the top and bottom parts, this makes it possible, by a simple mathematical difference operation, related or not to the number of cells, to make a continuous measurement of the cell respiration.

Other embodiments of the device are described further below.

Another object of the invention is the use of the culture device according to the invention for cell culture in suspension on microcarriers or on carriers. Indeed, when devices according to the invention are used in culture in carriers or microcarriers, the carriers or microcarriers are confined in said second culture zone. When the device is used for suspension cell culture, and therefore without carriers or microcarriers, the wall provided with an orifice is a membrane permeable to the medium but not permeable to the cells. The size of the pores of this membrane is a function of the all size. The invention also relates to the use of the culture device according to the invention for producing recombinant products, viruses, metabolites and the like.

Recombinant products means proteins of interest for research in the pharmaceutical sector, therapeutic or prophylactic molecules, antibodies, plasmids or any other molecule able to be produced by cells in culture, whether this be production by secretion or intracellular production.

The invention also relates to a method of culturing cells in a culture vessel with circulation of the culture medium, comprising:

introduction of culture medium into culture medium circulation means, discharge of culture medium from said culture medium circulation means, at least one first transfer of culture medium into a first culture medium upward transfer zone, at least one second transfer of culture medium into a second cell culture zone.

This method is characterised in that it also comprises:

at least one third culture medium transfer subsequent to said first culture medium transfer into a third culture medium transfer zone, by overflowing from the first culture medium transfer zone to the third culture medium transfer zone, at least one fourth culture medium transfer subsequent to said second culture medium transfer into a fourth culture medium transfer zone, by overflowing from the second culture zone into the fourth culture medium transfer zone, and in that said second culture medium transfer is a downward culture medium transfer.

As mentioned above, unlike the culture method of the U.S. Pat. No. 5,501,971, the culture medium travels through the culture zone upwards, which prevents the accumulation of cells in the bottom of the culture zone and reduces the pressure forces on the cells. The culture method according to the invention is therefore a particularly innovative method which allows culturing without a dead zone and without any place where cells accumulate whilst permitting culturing at very high efficiency.

Advantageously, the method also comprises an oxygenation of the culture medium during one or more of said transfers.

Said oxygenation preferably occurs through a direct gas-liquid contact during one or more of said transfers.

In a particular embodiment, the oxygenation is carried out during the fourth culture medium transfer, said fourth culture medium transfer being a flow of said culture medium along a flow wall.

In an advantageous embodiment, the method, in order to stabilise the film, provides for the addition of additives to the culture medium in order to modify the rheological properties of the water such as the additives included in the group consisting of surfactants, Pluronic F68, glycerine, quaternary ammoniums and any other additive for modifying the rheological properties of the culture medium.

Also advantageously, the flow of the culture medium is a flow along a hydrophilic wall.

Other embodiments of the method according to the invention are indicated in the accompanying claims.

Other characteristics, details and advantages of the invention will appear more clearly in the light of the following description, of particular non-limiting embodiment of the invention, while referring to the accompanying drawings.

BRIEF DESCRIPTION OF THE DRAWINGS

FIG. 12 shows a particular embodiment with a closed element 36b positioned above opening 36a.

FIG. 13 shows a particular embodiment with a flow regulating element 36c positioned above opening 36a.

Figure 1:
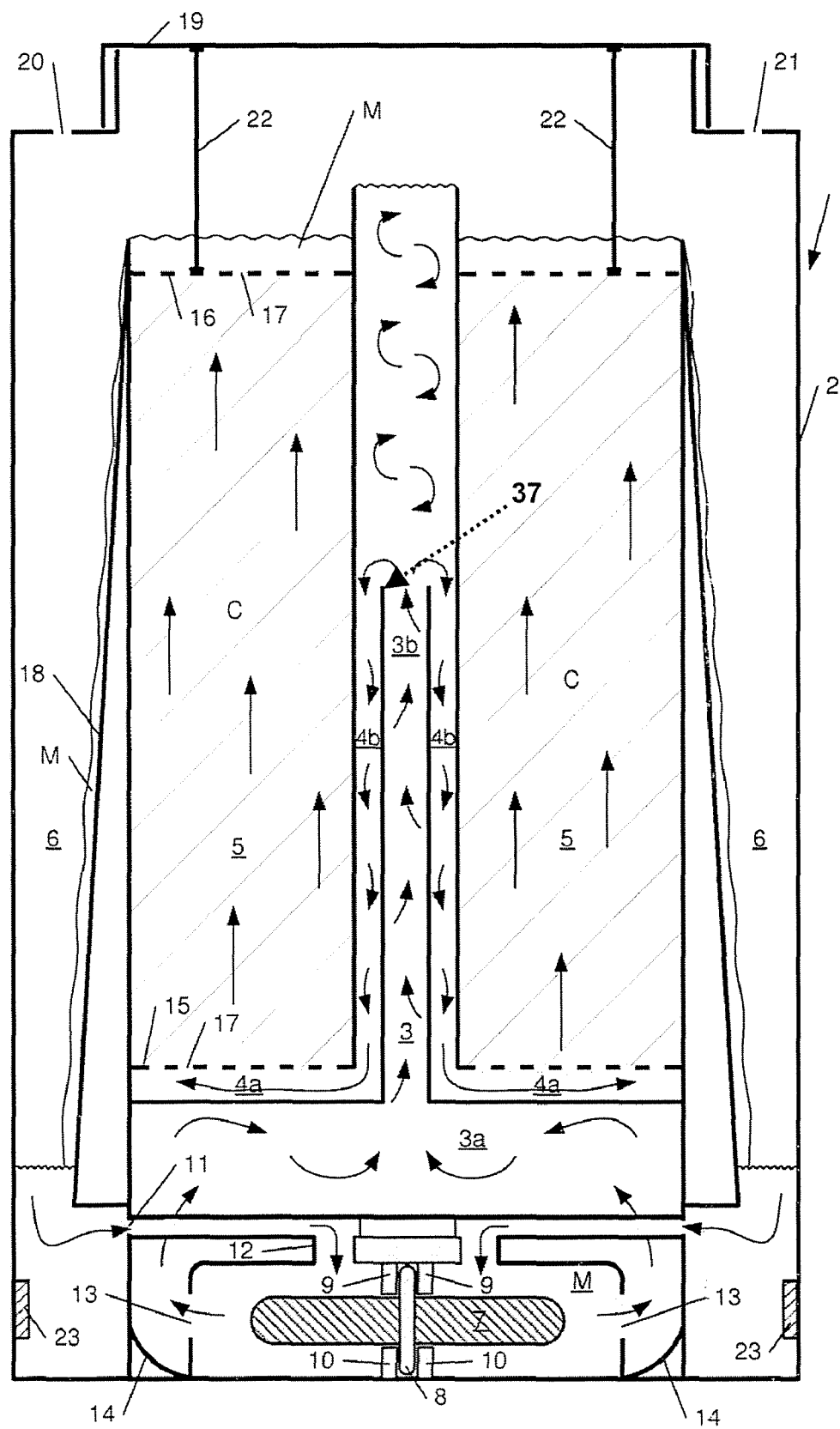
FIG. 1 is an outline diagram of a culture device according to an embodiment of the invention.

In the drawings, a same or similar reference sign has been allocated to a same or analogous element.

As can be seen in FIG. 1, the culture device 1 comprises a substantially vertical and cylindrical culture vessel 2, although other forms can also be envisaged according to the invention, for example any prismatic shape, preferably regular. The culture vessel comprises at least four zones in communication with one another. From the centre of the vessel towards the outside, the vessel comprises a first zone 3, a third zone 4a, 4b, a second zone 5 and a fourth zone 6.

The zone comprising cells has been hatched and comprises the letter C whilst the medium is shown by the letter M.

The culture vessel 2 comprises medium circulation means in its bottom part. The medium circulation means are, in this preferential embodiment, composed of a magnetic device 7, for example a magnetic bar 7 in rotation about a central rotation axis 8, real or virtual, a first end of which is housed in a top engagement means 9 and a second end of which is housed in a bottom engagement means 10. The magnetic bar is driven by a rotary magnetic drive motor external to the culture vessel 2 and which is not shown here. The circulation means comprise at least one medium inlet 11. The medium inlet 11 comprises at least one first end which ends in a diversion baffle 12 for the flow of medium. The magnetic bar functions as a centrifugal pump, that is to say the medium is sucked into a relatively central zone by the movement of the medium created by the bar and the medium is propelled outwards with respect to the central point. The medium diversion baffle 12 guides the medium in the relatively central zone of the bar so that the medium is sucked therein and is then propelled outwards. Advantageously, the inlets are in the same plane (star configuration) and the number of inlets 11 will be a number such that their positions will exhibit symmetry. More particularly, if three inlets are considered, it is advantageous for them each to be separated from one another by an angle of approximately 120°, if the number of inlets equal 4, the inlets will be separated from one another by an angle substantially equivalent to 90°, if the number of inlets is equal to 10, the inlets will be disposed with a separation angle approximately equal to 36°.

The medium circulation means also comprises at least one medium outlet 13. The medium outlet 13 is advantageously situated at the point where the medium is propelled by the centrifuge effect of the magnetic bar.

Advantageously, the number of outlets 13 will be a number such that their positions will exhibit symmetry. More particularly, if three outlets are considered it is advantageous for them each to be separated from the other by an angle of approximately 120°, if the number of outlets is equal to four, the outlets will be separated from one another by an angle substantially equivalent to 90°, if the number of outlets is equal to 10, the outlets will be disposed with a separation angle of approximately 36°.

Preferably, the outlets are not situated in the same horizontal plane as the inlets. The bottom part of the culture vessel comprises at least one medium guiding means 14, adjacent to said at least one outlet 13, which guides the culture medium propelled towards to the top of the culture vessel 2.

The first zone 3 of the culture vessel 2 is a substantially central zone and is a medium transfer zone. The first zone 3 comprises a basal part 3a and in particular embodiments optionally also a cylindrical part 3b. The diameter of the basal part 3a is less than the diameter of the culture vessel 2. The basal part 3a is in medium communication with said at least one medium outlet 13 of the medium circulation means. The basal part 3a is reduced in the top part of the first zone 3 to a cylinder 3b with a smaller diameter than the basal part 3a. The top cylindrical part 3b comprises an external wall and is in direct medium communication with the basal part 3a of said first medium transfer zone.

The third zone 4 is a medium transfer zone, external to the first medium transfer zone 3. The third zone also comprises a substantially basal part 4a (in the form of a sleeve) and in particular embodiments optionally also a substantially cylindrical top part 4b.

The substantially cylindrical part 4b of the third medium transfer zone 4 is essentially concentric with the substantially cylindrical part 3b of the first medium transfer zone 3 and these two parts are in medium communication. The medium communication is achieved by means of an orifice or a tube, by overflowing (as shown in the figure) via overflow (37) or any other possible means for achieving this communication. The second zone 5 is a cell culture zone, with or without carriers or microcarriers.

The second zone 5 is also in the form of a sleeve, at the centre of which re the first and third medium transfer zones 3 and 4.

The second zone 5 comprises a bottom wall 15 and a top wall 16, each wall 15 and 16 being provided with orifices 17 allowing a transfer of cultured medium essentially free from cells. The second culture zone 5 is in medium communication with the relatively basal part 4a of the third medium transfer zone 4 by means of orifices 17 in the bottom wall 15 allowing the medium to pass.

The fourth zone 6 is a medium transfer zone, external to the second culture zone 5 but internal to the culture vessel 2. The fourth zone 6 is in medium communication with the second culture zone 5. It is also in medium communication with the medium circulation means, via said at least one inlet 11. The medium communication is achieved by means of an orifice or a tube, by overflowing or by any other possible means for achieving this communication.

The particular embodiment described here comprises a substantially cylindrical culture vessel, but other embodiments can also be envisaged, as mentioned previously, for example a substantially prismatic vessel, preferably regular. Obviously, this is also the case with the various medium and culture transfer zones. They can also be prismatic, preferably regular, any combination of shapes being possible. In this case, the term sleeve must be envisaged as an envelope with a cross-section similar to the cross-section of the prism envisaged.

When the medium circulation means are in operation, the medium leaves them through said at least one outlet 13, when there are several of them, through the various outlets 13, and is diverted by the guiding means 14, it ends up in the substantially basal part 3a of the first medium transfer zone 3. The structure of the first medium transfer zone 3 and the output of the pump require the medium to be directed towards the substantially cylindrical part 3b of the first medium transfer zone 3. When it reaches the top of the wall of the substantially cylindrical part 3b, it overflows via overflow (37) into the third medium transfer zone 4.

The direction of circulation of the medium M is shown by the arrows in the figures.

It is clear to the skilled in the art that, in this particular embodiment, the wall of the substantially cylindrical part 3b of the first medium transfer zone 3 is less high than the wall of the third medium transfer zone 4 for reasons of efficiency and flow rate, but he will easily understand that the wall of the substantially cylindrical part 3b of the first medium transfer zone 3 can also be higher than the wall of the substantially cylindrical part 4b of the third medium transfer zone 4.

The medium is therefore subjected to the flow rate imposed by the pump and to gravity, it is directed downwards from the third medium transfer zone 4 running down the substantially cylindrical part 4a and reaches the substantially basal part 4b of the third medium transfer zone 4. Next the flow of medium has a rising direction through a communicating vessels effect by the imposed flow rate of the pump and reaches the top of the second culture zone 5. The medium reaches the second culture zone 5 from the third medium transfer zone 4 via the orifices for the passage of medium substantially free from cells 17 in the bottom wall 15 of the second culture zone 5.

As already mentioned above, the medium passage orifices 17 are sized according to the type of culture. If the culture is a culture without carrier, the wall 15 or 16 comprising orifices 17 will be a porous membrane where the pore size is less than the diameter of the cells. If the culture is on microcarriers or on carriers, the size of the orifices 17 will be less than the size of the microcarriers or carriers.

When the medium flow edge reaches the top of the wall of the second culture zone 5, it overflows into the fourth medium transfer zone 6. Naturally, if orifices are present or a tube, it must be understood that, when the medium flow edge reaches the orifice or tube, it flows into the fourth zone 6.

In the particularly preferential embodiment of the invention, the fourth medium transfer zone 6 comprises an inclined wall 18 on which the medium flows when it passes from the second zone 5 to the fourth zone 6. The inclined wall preferably comprises a hydrophilic membrane in order to improve the formation of the film on said inclined wall 18. The film must preferably be laminar in order to prevent as far as possible the formation of foam. In order to stabilise the film, it is also possible to add additives to the culture medium in order to modify the rheological properties of the water, in particularly of the culture medium, such as the additives included in the group consisting of surfactants, Pluronic F68, glycerine, quaternary ammoniums and any other additive for modifying the rheological properties of the culture medium.

The hydrophilic membrane will for example be a membrane consisting of polyoxyethylene.

The formation of the film on the inclined wall is an important step since it allows oxygenation on "thin film". Indeed the gaseous volume with respect to the quantity of medium in this fourth medium transfer zone is large and improves exchanges. In addition, the formation of the film on an inclined wall increases the gas-liquid contact surface area.

As can be seen in FIG. 1, the culture vessel preferably comprises a cover 19 through which at least one gas inlet orifice 20 and at least gas outlet orifice 21 pass. The gas inlet orifice 20 is preferably situated so as to communicate directly with the fourth medium transfer zone 6. In some variants, it may be preferable for the gas inlet orifice 20 to be present on the vertical wall of the culture vessel 2 or at the bottom of the culture vessel 2, that is to say the gas passes by means of an orifice 20 through the wall of the culture vessel 2 opposite to the cover 19, and for this orifice 20 to be provided with a tube in order to end above the liquid level (see FIG. 9).

In this embodiment, the cover 19 is fixed by fixing means 22 to the top wall 16 of the second culture zone 5. In variants, the cover 19 can be made an integral part of the top wall 16 of the second culture zone 5, this part opening when the cover 19 of the culture vessel 2 is raised. In this way, it is easy to take off a cell sample with or without carriers in order for example to evaluate the cell density, the structure of the cells and other physical characteristics of the cell which reflect the health of the culture. Indeed, connecting the two together makes it possible to open the culture compartment 5 simply by raising the cover 19 of the culture vessel 2.

In the case of culture in suspension, it could be advantageous to connect a porous membrane to the top wall 16 provided with orifices 17 of the second culture zone 5, this assembly can improve the rigidity of the cover/membrane assembly for taking samples.

Figure 2:
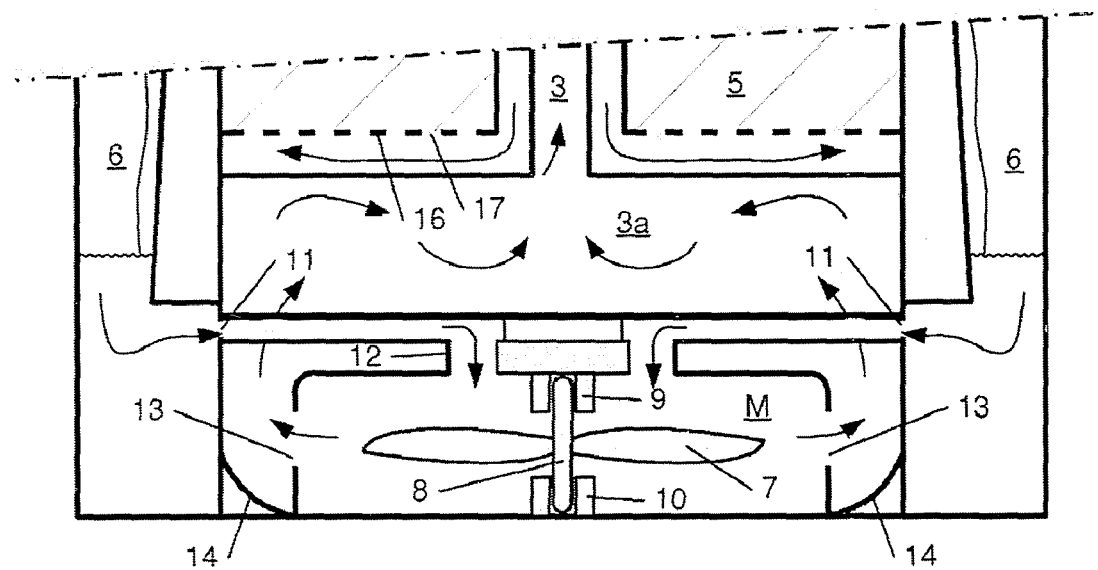
FIG. 2 is an outline diagram of a variant of the medium circulation means.

FIG. 2 illustrates a variant of the magnetic device of the medium circulation means. Here the magnetic bar 7 has the shape of a helix. The design of the magnetic device 7 with a substantially central rotation axis 8 will depend essentially on the volume of the culture. Indeed, for small cultures, the invention sets out to be able to us a simple bar such as a magnetic chip for circulating the medium. For large volumes, the invention envisages a magnetic rotor, also driven by an external motor, for example rotors like the ones used in aquariums which allow high medium circulation rates.

It can also, according to the invention, be envisaged using bubble production devices (not shown), more commonly referred to as "spargers" or "microspargers" according to the size of bubble produced.

Advantageously, when bubbles will be used, the pierced end of the bubble production device, for example of the tube, will be immersed in the medium at the bottom of the fourth medium transfer zone or in the first medium transfer zone. When this type of oxygenation is chosen, it is always also possible to continue the oxygenation on thin film, which makes it possible to reduce the flow of gas and to form fewer bubbles and therefore to reduce the formation of foam. In this case, provision is also made for having two gas inlets in the cover of the culture vessel or on the vertical wall of the latter. In addition, it is also possible to envisage that the bubble production device be present solely as an SOS procedure, and used solely when necessary.

The culture device also comprises a series of culture parameter sensors 23, for example for the dissolved oxygen partial pressure pO2, acidity pH, temperature, cloudiness, optical density, glucose, CO2, lactate, ammonium and any other parameter normally used for monitoring cell cultures. These sensors are preferably optical sensors which do not require connections between the inside of the culture vessel and the outside thereof. The preferential position of these sensors 23 is a critical position in that it is advantageous for these to be situated close to the wall of the culture vessel 2, for them to be in contact with the medium M and preferably in strategic positions, as in the zone through which the medium M passes before it passes through the cells or just after.

In fact, the invention contemplates particularly procuring a disposable bioreactor for all the reasons of simplicity and economy mentioned previously. Consequently, this is why the connections between the inside and the outside of the culture vessel have been reduced. In addition, the bioreactor according to the invention also envisages procuring a particularly reliable bioreactor in which the risks of contamination are particularly low by being disposable.

Figure 3:
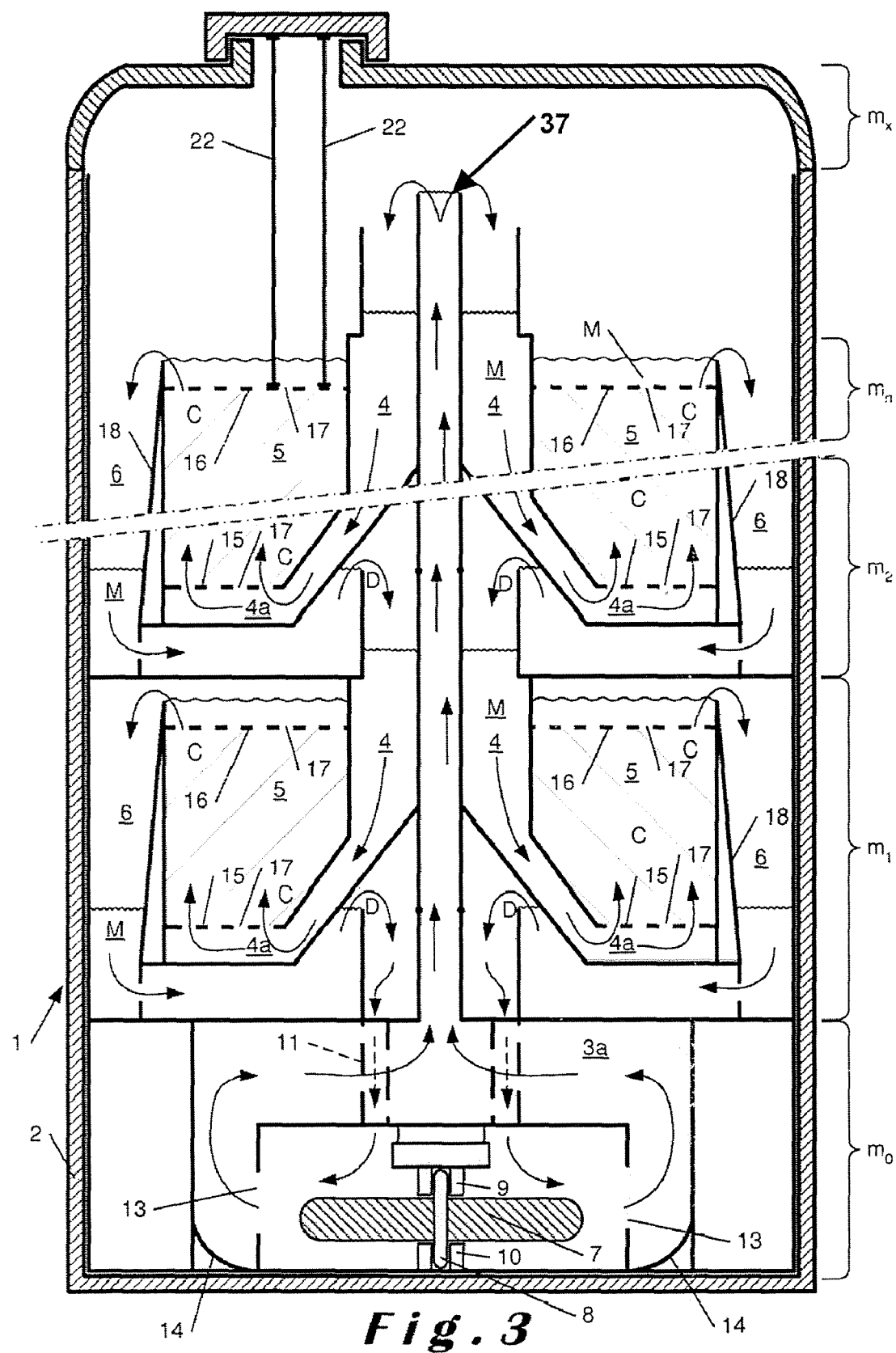
FIG. 3 is an outline diagram of a culture device according to the invention comprising several successive culture zones, particularly adapted for a scaling up.

As can be seen in FIG. 3, an embodiment of a device according to the invention also envisages a modular design which comprises a series of modules for cultures on a larger volume. For example, with this type of modular design, culture volumes of around 500 ml to 100 liters are for example envisaged, through the use of a very limited number of standard modules.

According to the invention it is envisaged providing a series of modules that can be "slipped" around the first medium transfer zone 3 to be placed in a standard culture vessel 2 comprising medium circulation means and a cover 19.

In a particularly flexible variant, the invention sets out to procure a mounting system which comprises various standard modules. These standard modules are for example a circulation means module to be placed at the bottom of the assembly, one or more culture modules and a cover module. According to the invention, although other means of fixing these modules can be envisaged, the modules will be clamped on one another, for example by means of rapid connectors perfectly impermeable from the liquid and gaseous point of view.

Consequently, according to the type of culture and the required volume, the user will be able to take from his stock a base module comprising the medium circulation means, he will also have to take therefrom the number of culture modules that he requires according to the required culture volume and then take a head module corresponding to the cover. Next, all these modules being packaged in sterile fashion, he will merely need to unpack them and "clip" them one above the other. The stacking can form the "disposable bioreactor" or can be placed in an appropriate vessel.

FIG. 3 therefore illustrates an embodiment of the modular culture device according to the invention.

The culture device 1 comprises a culture vessel 2 which comprises medium circulation means like those explained in detail in FIG. 1. The base module $m_0$ comprising the circulation means can be fixed to the bottom of the culture vessel 2 or can also be slid into the culture vessel 2 (the embodiment depicted) in order to be able to dispose it and to use another one for another culture and thus prevent cross contaminations.

The base module $m_0$ comprises the circulation means. As in FIG. 1, these circulation means comprise a magnetic device 7, rotating about a central rotation axis 8, a first end of which is housed in a top engagement means 9 and a second end of which is housed in a bottom engagement means 10. The circulation means comprise at least one medium inlet 11. The medium circulation means also comprise at least one medium outlet 13. The base module $m_0$ of the culture vessel comprises at least one medium guiding means 14 adjacent to said at least one outlet 13, which guides the culture medium propelled towards the top of the culture vessel 2.

The culture vessel 2 comprises a series of culture modules ($m_1, m_2, \ldots, m_n$) which are, in this embodiment, stacked one above the other. It could also be envisaged that they be simply adjacent to one another, that is to say placed side by side. In the embodiment illustrated in FIG. 3, the modules are clamped to one another by means of rapid connectors 24 or clips.

Each culture module $m_1, m_2, \ldots, m_n$ comprises a first 3, a second 4, a third 5 and a fourth zone 6. These zones 3, 4, 5, 6 have each the same function as that mentioned in FIG. 1.

In addition, it may be advantageous for each module to comprise a gas or gas mixture inlet (not illustrated) in communication with the fourth zone 6 of each culture module. The vessel may also comprise for its part an outlet for the excess gas or gas mixture (not illustrated). For example, the gas inlet orifice may be present at the bottom of the culture vessel 2, that is to say the gas passes by means of an orifice through the wall of the culture vessel 2 opposite to the cover 3 and this orifice 20 is provided with a tube in order to end above liquid level (see FIG. 9) of the module $m_1$. Consequently, the gaseous mixture reaches the fourth medium transfer zone 6 of this module. The module $m_2$ placed above the module $m_1$ can also comprise a tube which enables the gaseous mixture present in the fourth zone 6 of the culture module $m_1$ to communicate with the fourth zone 6 of the module $m_2$. This tube therefore advantageously passes through the bottom wall of the module $m_2$.

In certain embodiments, for long duration culture, it may be advantageous to replace part of the culture medium with fresh medium or to carry out an addition of nutriment. Consequently, the base module $m_0$ can then comprise a nutriment inlet (not illustrated). Also advantageously, the culture vessel can comprise, at the medium circulation means, a medium outlet (not illustrated) in order to prevent overflowing.

In a similar manner, the culture vessel 2 comprises a head module comprising a cover 19, advantageously connected to a top wall 16 provided with medium passage orifices 17 by fixing means 22 in order to simplify taking samples in the module $m_n$ situated above, as in FIG. 1.

In addition, advantageously culture parameter sensors can also be provided in each culture module. It is also possible to provide sensors in only one or several culture modules at all zones or in the base module.

In the embodiment illustrated in FIG. 3, the medium circulates in the following manner. To simplify the explanation, we will use only two culture modules $m_1$ and $m_2$ and a base module $m_0$, but it is certain that the culture device according to the invention can comprise a very large number of them.

In the base module $m_0$, the medium is propelled from the medium circulation means M via said at least one outlet 13, when there are several of them, through the various outlets 13 and is diverted by the guiding means 14. It ends up in the substantially basal part 3a of the first medium transfer zone 3. The substantially basal part 3a of this embodiment is a zone common to all the culture modules and, in the embodiment illustrated, is situated in the base module. This is valid whether the culture modules are stacked or juxtaposed.

The structure of the first medium transfer zone 3 of an embodiment of a device according to the invention and the output of the pump require the medium to be directed towards the substantially cylindrical part 3b of the first medium transfer zone 3 of the first module $m_1$; towards the substantially cylindrical part 3b of the first medium transfer zone 3 of the second module $m_2$.

In this embodiment, it is the assembling of the modules which creates a large first medium transfer zone 3 comprising a substantially cylindrical part 3b.

When the medium reaches the top of the wall of the substantially cylindrical part 3b of the second culture module $m_2$, it overflows into the third medium transfer zone 4 of the second culture module $m_2$.

The direction of circulation of the medium M is shown by arrows.

The medium is therefore subjected to the flow rate imposed by the pump and to gravity, it is directed towards the bottom of the third medium transfer zone 4 of the second culture module $m_2$, flowing down the substantially cylindrical part 4a of the second culture module $m_2$, and reaches the substantially basal part 4b of the third medium transfer zone of the second culture module $m_2$. Next, the flow of medium has a rising direction through a communicating vessels effect and through the imposed flow rate of the pump and reaches the top of the second culture zone 5 of the second culture module $m_2$. The medium reaches the second zone 5 of the second culture module $m_2$ from the third medium transfer zone 4 of the second culture module $m_2$ via the orifices for the passages of medium substantially free from cells 17 of the bottom wall 15 of the second culture module $m_2$.

When the medium flow edge reaches the top of the external wall of the second culture zone 5 of the second culture module $m_2$, it overflows into the fourth medium transfer zone 6 of the second culture module $m_2$. Naturally, if orifices or a tube are present in this external wall of the culture zone 5, it is necessary to understand that, when the medium flow edge reaches the orifice or tube, it flows into the fourth zone 6 of the second culture module $m_2$. In the particularly preferential embodiment of the invention, the fourth medium transfer zone 6 of the second culture module $m_2$ comprises an inclined wall 18 on which the medium flows when it passes from the second zone 5 of the second culture module $m_2$ to the fourth zone 6 of the second culture module $m_2$. The inclined wall preferably comprises a hydrophilic membrane in order to improve the formation of the film on said inclined wall 18. The film must preferably be laminar in order to prevent as far as possible the formation of foam. In order to stabilise the film, it is also possible to add additives to the culture medium in order to modify the rheological properties of the water, as mentioned before.

Next, the culture medium present in the fourth medium transfer zone 6 of the second culture module $m_2$ overflows either through a tube or over the top (D) of the wall of the fourth medium transfer zone 6 of the second culture module $m_2$ into the third medium transfer zone 4 of the first culture module $m_1$.

The medium is therefore subjected to the flow rate imposed by the pump and to gravity, it is directed downwards from the third medium transfer zone 4 of the first culture module $m_1$, flowing down the substantially cylindrical part 4a of the first culture module $m_1$, and reaches the substantially basal part 4b of the third medium transfer zone of the first culture module $m_1$. Next, the flow of medium has an upward direction through a communicating vessels effect and through the flow rate imposed by the pump and reaches the top of the second culture zone 5 of the first culture module $m_1$. The medium reaches the second zone 5 of the first culture module $m_1$ from the third medium transfer zone 4 of the first culture module $In_1$ via the orifices for passage of medium substantially free from cells 17 in the bottom wall 15 of the first culture module $m_1$.

When the medium flow edge reaches the summit of the wall of the second culture zone 5 of the first culture module $m_1$, it overflows into the fourth medium transfer zone 6 of the first culture module $m_1$. Obviously, if orifices or a tube are present in this wall, it must be understood that, when the medium flow edge reaches the orifice or the tube, it flows into the fourth medium transfer zone 6 of the first culture module $m_1$.

The fourth medium transfer zone 6 of the first culture module $m_1$ can also comprise an inclined wall 18 on which the medium flows when it passes from the second culture zone 5 of the first culture module $m_1$ to the fourth medium transfer zone 6 of the first culture module $m_1$. The inclined wall is possibly provided with a hydrophilic membrane as above.

Next, the medium returns to the base module $m_0$ and to the medium circulation means through the inlet (pipe) 11, that is to say the culture medium present in the fourth medium transfer zone 6 of the first culture module $m_1$ overflows either via a tube or over the top of the wall of the fourth medium transfer zone 6 of the first culture module $m_1$ in a pipe 11 which ends in a substantially central zone of a siphon created by said centrifugal pump which constitutes the medium circulation means according to the invention of the base module $m_0$.

Figure 4:
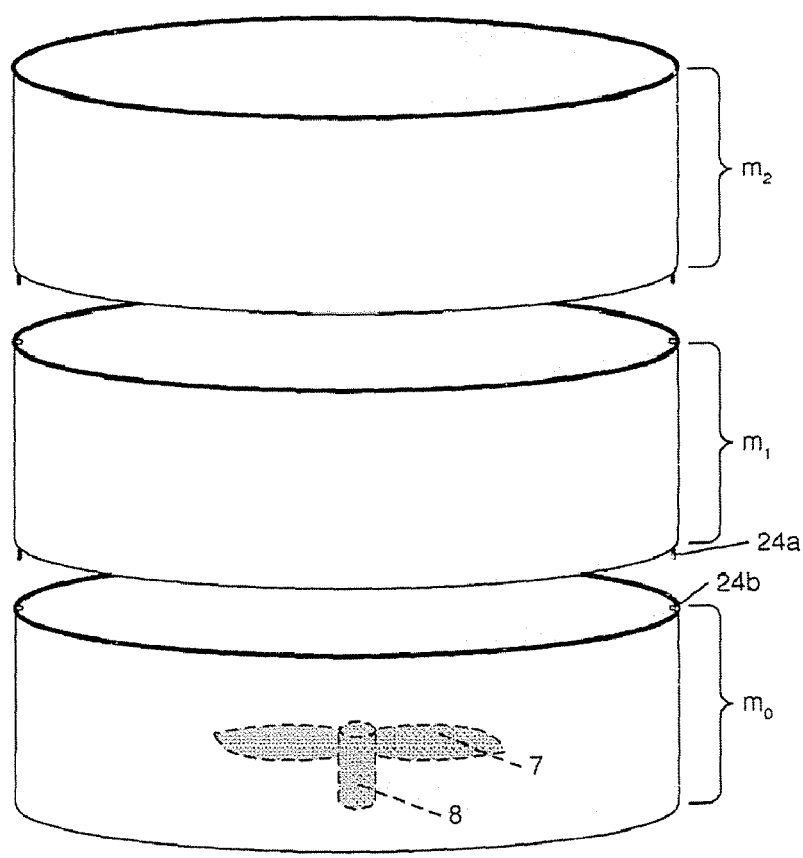
FIG. 4 illustrates highly schematically a variant of FIG. 3.
Figure 9:
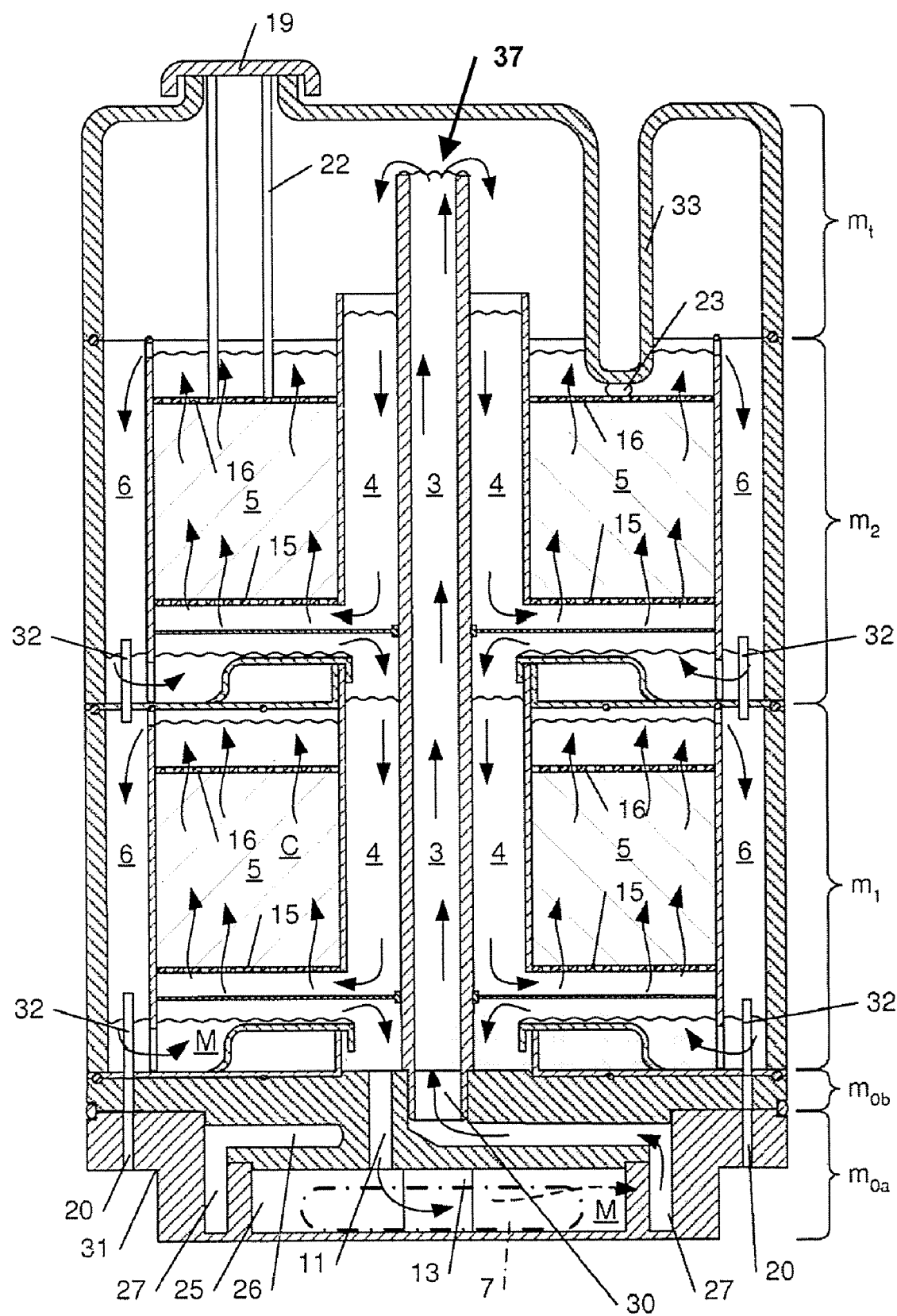
FIG. 9 is a transversal section of the culture device according to the invention produced by an assembly of modules, in particular disposable modules.

In a variant of this embodiment, illustrated highly schematically in FIG. 4 and in detail in FIG. 9, the stacked modules m constitute the culture vessel. In this variant of FIG. 4, there can exist for example three kinds of module, base modules $m_0$, modules $m_1$; $m_2$, ..., n comprising the four zones and a head module $m_x$ (not shown). The base module $m_0$ or basal module $m_0$ comprises medium circulation means and assembly means, it is designed to engage the first assembly means 24a of a four zones module $m_{1, 2, ..., n}$ as explained above, and to constitute the bottom of the vessel. The head module $m_t$ is designed to engage the second assembly means 24b of a four zones module $m_{1; 2, ..., n}$. The four zones module $m_{1; 2, ..., n}$ engaged by the base module $m_0$ can be the same as that engaged by the head module $m_t$ or the four zones module $m_{1; 2, ..., n}$ engaged by the base module $m_0$ can be the first in a series of four zones modules $m_{1; 2, ..., n}$ and the one engaged by the head module $m_t$ is consequently the second four zones module in said series of four zones modules $m_{1; 2, ..., n}$.

This variant functions in the same way as that explained in detail for FIG. 3.

Figure 5:
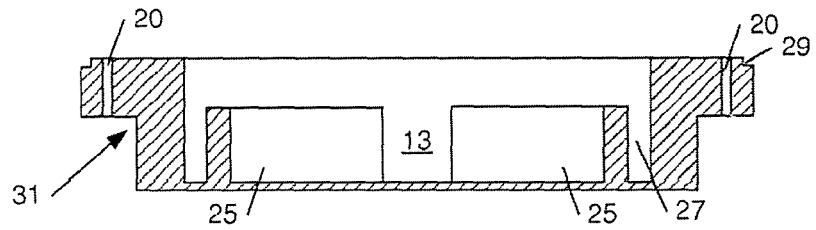
FIG. 5 is a transversal section of a bottom part of the base module confining the medium circulation means of a preferred embodiment of devices according to the invention.
Figure 6:
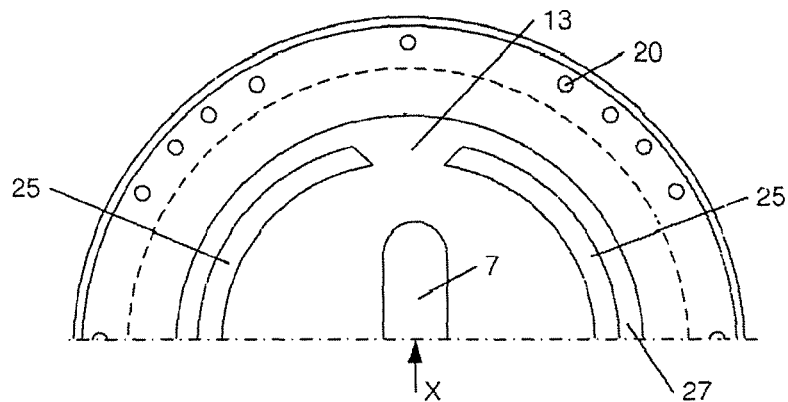
FIG. 6 is a top view of the bottom part of the base module confining the medium circulation means as illustrated in FIG. 5.

FIGS. 5 and 6 illustrate half of the basal part of the base module $m_0$. FIG. 5 is a cross-section view and FIG. 6 is a top view. As can be seen, the medium is designed to enter the base module through at least one inlet in a substantially central area represented by the letter x in the figures. The rotation axis of the magnetic device 7 passes through this centre x, whether it be real or virtual. When the circulation means are in operation, the magnetic device 7 is in rotation about its rotation axis, the rotation thereof creates a siphon which sucks the medium within the medium circulation means. The zone in which the magnetic device is in rotation is confined by baffles or walls 25. In this embodiment two baffles have been shown, but their number can be much greater, for example 3, 4, 5, 6, 8, 10, etc. The baffles will preferably be disposed symmetrically on the circumference defined by the whole of this.

The spaces 13 between the baffles 25 are medium outlet orifices. Indeed, the medium is sucked by the siphon created by the rotation of the magnetic device and the medium is expelled towards the outside of the zone delimited by the baffles 25, through the orifices 13 between the baffles. Since two baffles 25 have been shown, there are two medium outlet orifices in this embodiment but their number can be much greater, for example 3, 4, 5, 6, 8, 10, etc. As the baffles are preferably disposed symmetrically, the locations of the medium outlets 13 are also advantageously disposed symmetrically. When the medium is expelled by the outlets 13, it ends up in the essentially circular zone 27.

In this embodiment, the basal part of the base module $m_0$ has in it orifices 20, substantially tubular in shape, which are orifices allowing for example an introduction of gas or gas mixture, fresh medium, discharge of gas or mixture of gas, drawing off of medium, etc.

In addition, a recess 31 is provided for accessing these orifices 20 from the outside, which makes it possible to connect these orifices to a supply of gas or gas mixture, fresh medium, etc.

Figure 7:
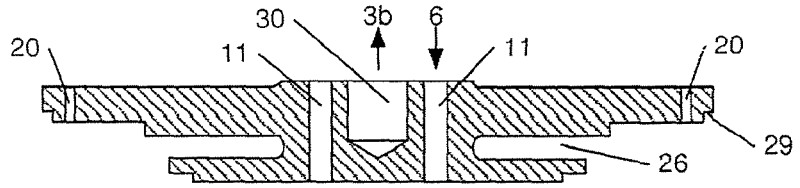
FIG. 7 is a transversal section of a top part of the base module confining the circulation means of the same preferred embodiment of devices according to the invention.
Figure 8:
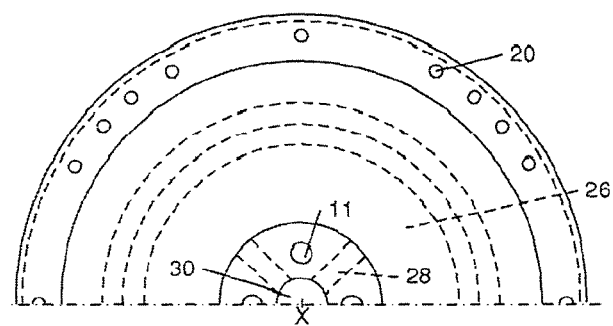
FIG. 8 is a top view of the top part of the base module confining the circulation means of a device as illustrated in FIG. 7.

FIG. 7 is a view in section of the top part of the base module $m_0$ according to the invention and FIG. 8 is a view from above of this same part. The top part comprises substantially tubular-shaped medium inlet orifices 11. These inlet orifices 11 guide the medium coming from the fourth medium transfer zone 6 of the device in the siphon created by the rotation of the magnetic device. When the magnetic device is in rotation, the medium situated in the essentially circumferential zone 27 depicted in FIGS. 5 and 6 enters the perforation 26, said perforation 26 being in communication with the conduits 28 enabling the expelled medium to reach a zone 30 in medium communication with the first medium transfer zone 3 of the device, in particular with the essentially tubular part of the first medium transfer zone.

The top part depicted in FIG. 7 is an element designed to be disposed on the bottom part depicted in FIG. 5. Naturally, this base module $m_0$ could also be obtained in another way, but for reasons of simplicity of production it has been produced for this embodiment in two parts that can be connected together. As can be seen moreover, the top part and the bottom part are connected together in a preferentially sealed manner at the recesses 29 illustrated in the two FIGS. 5 and 7.

All the illustrations of medium circulation means of the present application can also be produced in various ways. It goes without saying that all the ways for producing the various embodiments of the medium circulation means, confined or not in the base module, are included in the scope of the claimed protection.

Figure 10:
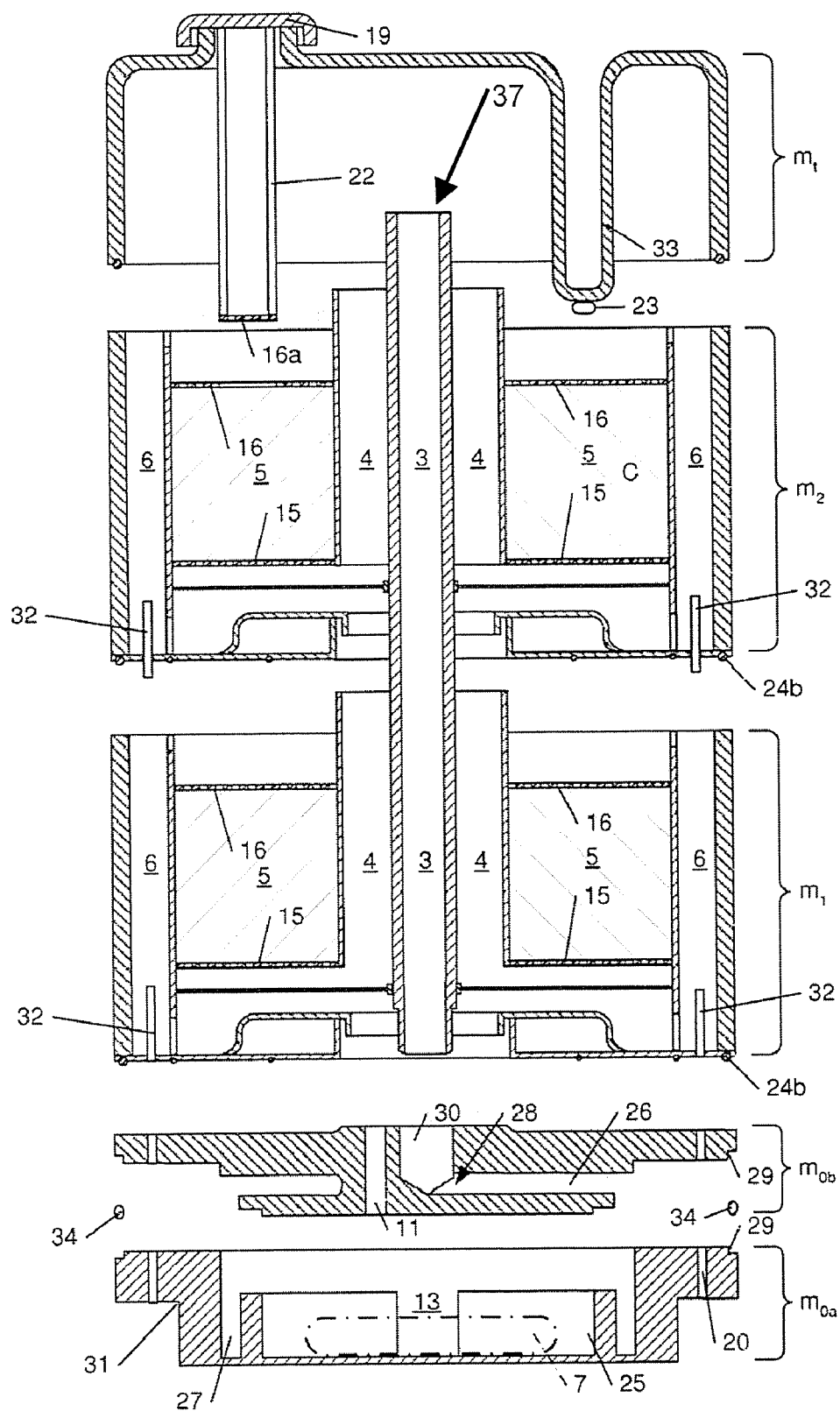
FIG. 10 is an exploded view of FIG. 9.

FIG. 9 is a cross section view of a particularly advantageous embodiment of a device according to the invention, whilst FIG. 10 is an exploded cross section view of the same embodiment. The exploded view gives a clear understanding of the particularly practical and inventive aspect of the present invention.

Consequently the two figures will be commented on at the same time. As can be seen, this embodiment of a device according to the invention consists, from bottom to top, of a clamped stack of the bottom part of the base module $m_0$ ($m_{0a}$) comprising a zone in which the magnetic device is in rotation which is confined by baffles 25. The space 13 between the baffles 25 visible in this figure is a medium outlet orifice. This is because the medium is sucked by the siphon created by the rotation of the magnetic device and the medium is expelled towards the outside 27 (essentially circular zone) of the zone delimited by the baffles 25 through the orifices 13 between the baffles 25, the top part of the base module $m_0$($m_0$b) comprising substantially tubular shaped medium inlet orifices 11. These inlet orifices 11 guide the medium coming from the fourth medium transfer zone in the siphon created by the rotation of the magnetic device 7. When the magnetic device is in rotation, the medium situated in the essentially circular zone 27 enters the perforation 26, said perforation 26 being in communication with the conduits 28 enabling the expelled medium to reach a zone 30 in medium communication with the first medium transfer zone 3, in particular with the essentially tubular part of the first medium transfer zone, a first culture module $m_1$ as explained in detail in the explanation of FIG. 3, a second culture module $m_2$ (see FIG. 3), a head module comprising a recess 33 provided with an optical sensor 23 immersed in the culture medium, a cover 19 comprising fixing means 22 connected to a part 16a of the top wall 16 of the second culture zone 5 of the second culture module $m_2$.

All the modules comprise fixing means 24a and 24b as illustrated schematically in FIGS. 4, 9 and 10. Each module comprises several of these, which, according to the required assembly, will be used or not, but this makes it possible to obtain a single culture module which can be assembled both with another culture module and with the base module or the head module. These fixing means are for example two concentric circles provided with a circular seal, rapid connectors well known in the art of cell culture, a screw pitch and a serration or any other device for assembling these modules according to the invention.

In this embodiment, the basal part of the base module $m_0$ is bond with orifices 20 substantially tubular in shape which are orifices allowing in this case an introduction of gas or gas mixture. The gas inlet orifice 20 is connected to a tube 32 which ends above the level of the culture medium, enabling the gas or gas mixture to reach at least a fourth medium transfer zone 6 of the culture device 1 according to the invention. All the ambient atmospheres of the fourth medium transfer zone 6 are connected by similar tubes 32 so that the gas mixture can reach the top. It is particularly advantageous in a device with modules stackable for height which can rise very high to provide a gaseous supply through the bottom of the reactor.

In a variant, the basal part comprises a gas or gas mixture feed tube for bringing the gaseous substance into the zone in which the magnetic device is situated. In this way, the incoming gas is stirred by the rotation of the magnetic device and the dissolution of the oxygen is improved by the movement of the medium. The excess gas is also stirred and moves upwards again in the form of small bubbles. This variant is also applicable to the embodiment illustrated in FIG. 1.

In addition, a recess 31 is provided for accessing these orifices 20 from the outside, which makes it possible to connect these orifices to a supply of gas, gas mixture, fresh medium, etc.

The top part mob of the module $m_0$ is an element designed to be gripped by virtue of the fixing means 28 and sealingly by virtue of the circular seal 34 on the bottom part $m_{Oa}$ of the base module $m_0$.

Naturally the present invention is in no way limited to the embodiments described above and many modifications can be made thereto without departing from the scope of the accompanying claims.

For example, the embodiment of a device according to the invention depicted in FIG. 1 can also comprise a nutriment feed, either in a tube through the cover, or a tube through one of the walls of the device. Likewise, heating means can also be present in the first or fourth zone of the device or of a module or each four zones module. Possibly, the device according to the invention can also comprise several medium circulation means, for example several centrifugal pumps.

The devices and methods of the present invention enable a homogenous flow of culture medium upon entry trough the orifices (17) in the bottom part (15) of the second zone (5) and consequently also during the further passage through this second zone (5). This in contrast to devices wherein the first zone (3) is in direct contact with the second zone (5) which results in a non-homogenous flow throughout the second zone (5). Such non-homogeneous flow results in the present of undersupplied or dead zones within the cell culture zone which are insufficiently supplied with oxygen and nutrients, and wherein cell growth and/or metabolism is far from optimal.

As described above in detail, a particular embodiment of the devices and methods described in the present invention relates to devices and their use, wherein the third zone (4) is a zone internal to said second zone (5) and external to said first zone (3) as depicted in FIG. 1. The flow of the medium from the basal part of the first zone (3a) upwards via the top cylindrical part of the first zone (3b), further downwards via the cylindrical top part (overflow 37) of the third transfer zone (4b) to the basal part of the third zone (4a) generates the desired homogeneous flow upon entry in the bottom part of the second zone (5).

The presence of the cylindrical parts 3b and 4b further allows an easy access to the medium for assaying its properties prior to entry in the second zone (5). The presence of a cylindrical element 4b also prevents that a high pressure is built up in the device. The presence of cylindrical parts 3b and 4b allows in addition the manufacture of a device comprising different modules as depicted in FIG. 3.

Figure 11:
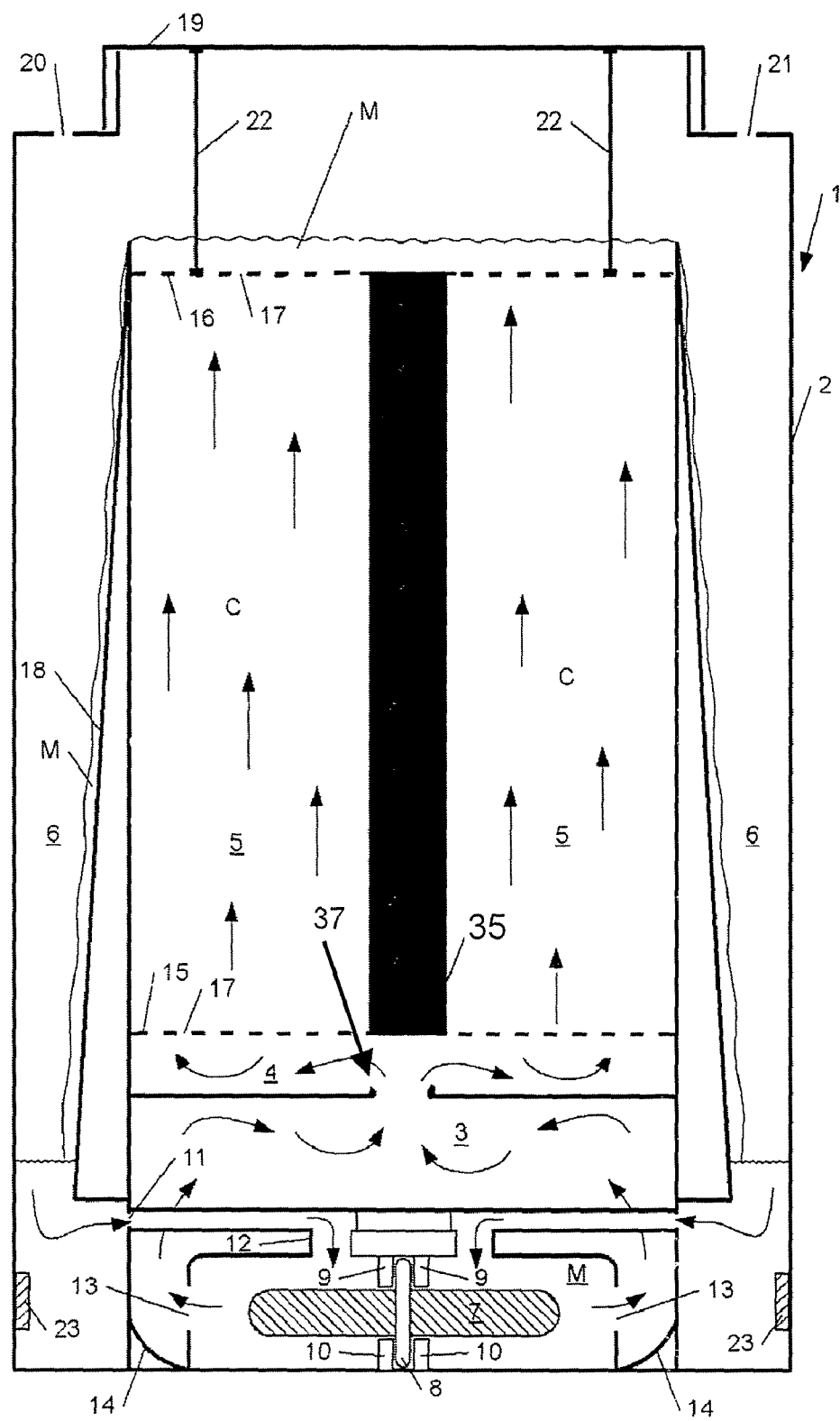
FIG. 11 is outline diagram of a culture device according to an embodiment of the invention, showing a solid element (35) within the second zone (5).

Other embodiments of the devices and methods described in the present invention relates to devices as depicted in FIG. 1 which are modified such in that the liquid flow through the cylindrical parts 3b and 4b is bypassed. In these alternative embodiments of devices of the present invention the third zone (4) is a located entirely below the second zone (5) and entirely above the first zone (3). FIG. 11 shows an embodiment of a device wherein the part of the device corresponding to the cylindrical parts of the first zone and the second zone (3b and 4b) in FIG. 1 are replaced by a solid element (35) in e.g a plastic, glass or metal.

In this device as depicted in FIG. 11 the first zone (3) and the second zone (4) consist of a flattened shaped volume corresponding respectively to the basal parts 3a and 4a as depicted on Figure A and lack the cylindrical parts 3b and 4b, shown in FIG. 1.

With this adaptation the culture medium can equally overflow from the first zone (3) to the third zone (4), via the overflow 37. The flow of the medium created by the stirring device (7) is rendered homogeneous by the separating wall between first zone (3) and third zone (4) and results in a homogeneous flow upon entry of the second zone (5).

In particular embodiments, as indicated in FIG. 11, the separating wall between the first zone (3) and the third zone (4) consist of a horizontal part as well as a of a vertical part, wherein this vertical part with the overflow has a height of about up to 5%, up to 10%, up to 20% or even up to 50% of the height of the third zone (4). In other particular embodiments, the vertical part of the separating wall between the first zone (3) and the third zone (4) is absent.

In particular embodiments the solid element 35 is provided with channels adapted to incorporate for example a probe to measure a condition of the medium in the third zone (4) (pH, oxygen, temperature, . . . ). In other particular embodiments, solid element 35 is provided with a channel comprising a safety pressure valve which can open when an excessive pressure is built up in the first zone (3) and third zone (4).

Figure 12:
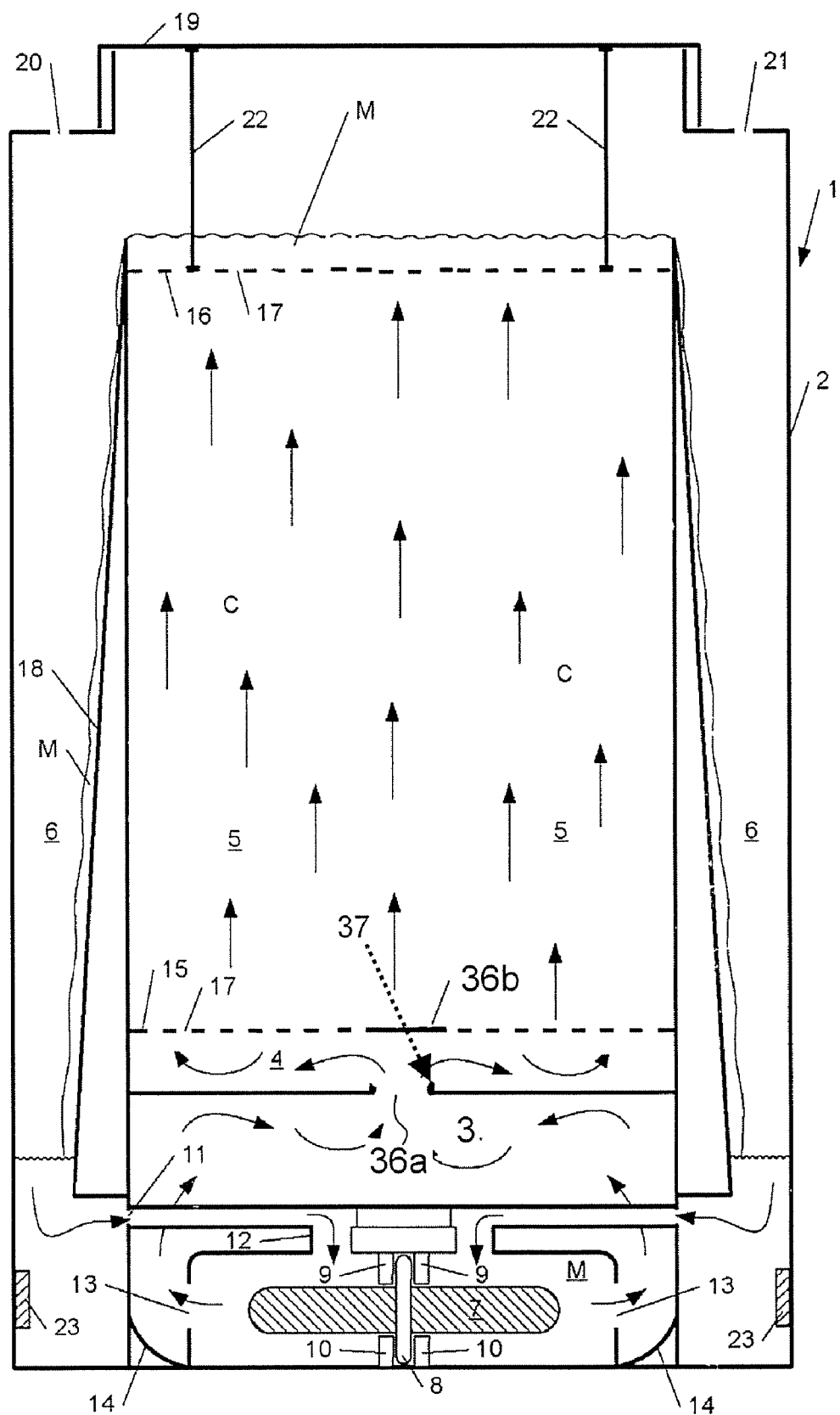
FIGS. 12 and 13 are outline diagrams of a culture device according to an embodiment of the invention, showing a second zone (5) which does not comprise internal to the second zone (5) portions of a first zone (3) or third zone (4).
Figure 13:
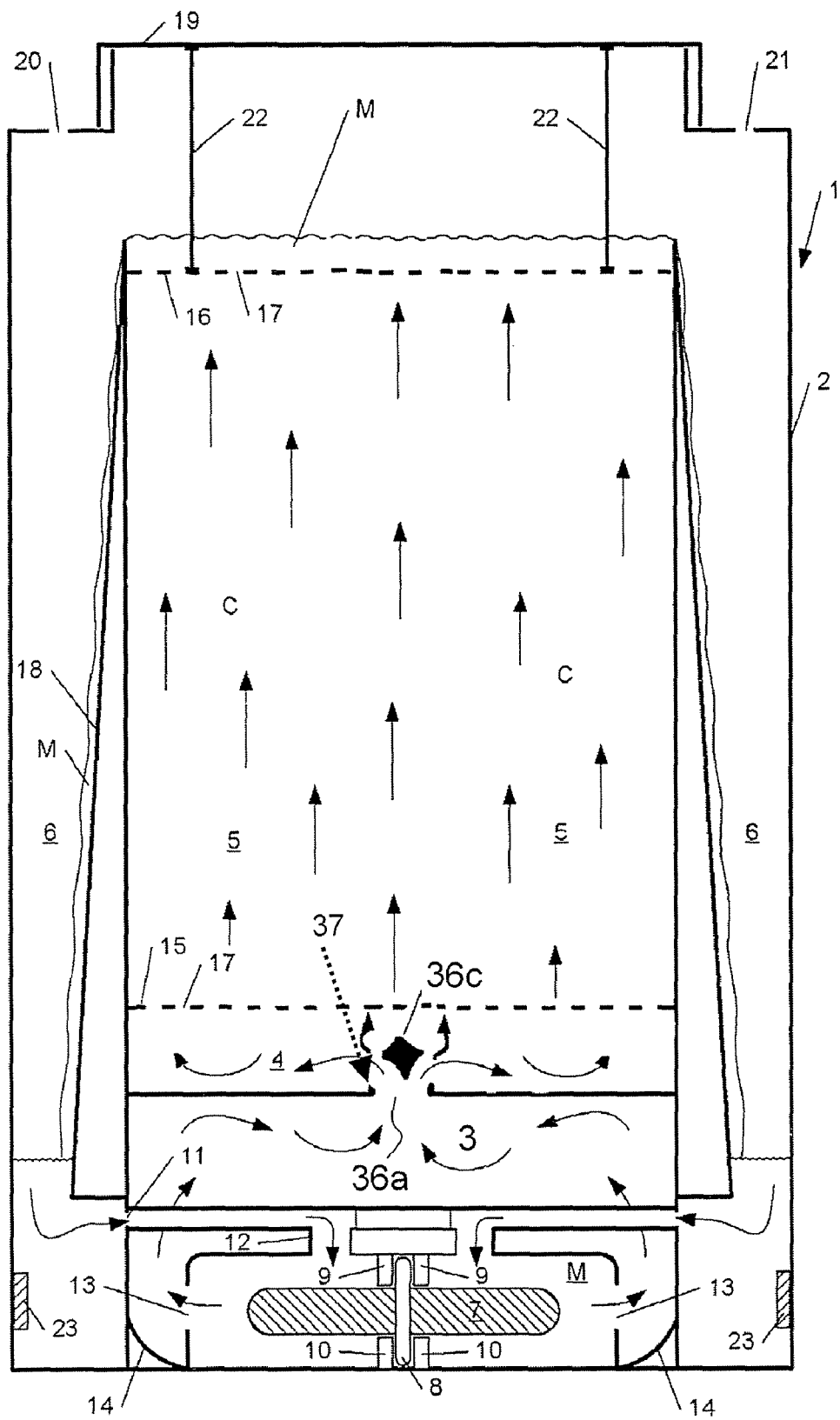

FIGS. 12 and 13 show yet alternative embodiments of a device wherein the cylindrical parts 3b and 4b of the respectively the first zone and the third zone second zone are absent compare to FIG. 1. The volume previously occupied by elements 3b and 4b, now becomes parts of the second zone (5) resulting a in more efficient use of the device resulting from the enlarged volume which is suitable for cell growth.

In order to prevent the direct inflow of medium from the first zone (3) into the second zone (5) without an homogenous flow distribution into the third zone (4), the orifices (17) in the bottom wall of the second zone (5) are closed at those regions (36b) which are located above an opening (36a) in the wall between the first and the third zone. The adaptation of the device by providing closed region 36b above opening 36a results in the overflow of the culture medium from the first culture medium transfer zone (3) into the third culture medium transfer zone (4) before it enters as a homogenous flow into the second zone (5).

FIG. 12 shows a schematic representation of a device wherein one central opening (36a) and corresponding closed region (36b) present. In particular embodiments, a plurality of openings (36a) and corresponding closed regions (36b) is provided into respectively the separating wall between first zone (3) and third zone (4), and into the wall between third zone (4) and second zone (5). Typically such plurality of openings (36a) and corresponding closed regions (36b) are distributed symmetrically.

In an alternative embodiment of the present invention, the homogenous flow of the medium is achieved by providing an flow redistributing element (36c) within the third zone (4) as indicate in FIG. 13. Such element can have any shape suitable for an appropriate redistribution of the medium coming from the first zone (3) to obtain a homogenous liquid flow in third zone (3) prior to entry in the second zone (5).

In a particular embodiment element 36c has the form of a set of radially extending rods with a circular, diamond or oval cross section, positioned above corresponding radially applied openings (36a).

LIST OF COMPONENTS 1. culture device
2. culture vessel
3. first culture medium transfer zone
3a basal part of the first culture medium transfer zone
3b top cylindrical part of the first culture medium transfer zone
4. third culture medium transfer zone
4a basal part of the third culture medium transfer zone
4b cylindrical top part of the third culture medium transfer zone
5. second culture zone
6. fourth culture medium transfer zone
7. magnetic device
8. central rotation axis
9. top engagement means
10. bottom engagement means
11. medium inlet
12. diversion baffle
13. medium outlet
14. medium guiding means
15. bottom wall of the second culture zone
16. top wall of the second culture zone
17. orifices in top and bottom walls of the second culture zone
18. inclined wall
19. cover of the culture vessel
20. gas inlet orifice
21. gas outlet orifice
22. means of fixing the cover to the top wall of the second culture zone
23. sensors
24. assembly means
24a. first assembly means
24b. second assembly means
25. baffles or walls of the base module
26. breakthrough in the base module
27. essentially circular zone
28. conduits
29. recesses for the circular seal
30. zone in medium communication with the first culture medium transfer zone
31. access recess to the orifices 20
32. gas feeding tube
33. recess in the cover for sensors
34. circular seal
35. solid element
36a. opening
36b. closed region
36c. flow redistributing element
37. overflow
$m_0$=base module
$m_1$ . . . to $m_n$=culture modules
$m_t$=head module
M=culture medium
C=cells
D=top of the wall of the fourth culture zone All publications and patent applications mentioned in this specification are herein incorporated by reference to the same extent as if each independent publication or patent application was specifically and individually indicated to be incorporated by reference.

Other embodiments are within the scope of the claims.

What is claimed is:

1. A device for culturing cells based on a vertical flow of a culture medium through a fixed bed of media, comprising: a culture vessel provided with a cover, wherein there is situated at least one first zone and at least one second zone, wherein said first zone is for transferring the culture medium essentially containing no cells and said second zone is for culturing cells, means of circulating the culture medium, allowing circulation of the culture medium through the second zone, said second zone comprising a bottom wall and a top wall, wherein each wall is provided with orifices allowing a transfer of culture medium essentially free from cells, and further comprising at least one third and at least one fourth zone, wherein both are essentially free from cells, wherein said third zone is in medium communication with the first and second zones and wherein said fourth zone is in medium communication with the second zone and with the first zone via the means for circulating the culture medium, and in that the means for circulating is adapted to circulate the culture medium from bottom to top in said second zone;

wherein the culture vessel is arranged such that the culture medium overflows from the first zone to the third zone, and overflows from the second zone to the fourth zone.

2. The device according to claim 1, wherein said third zone is a zone internal to said second zone and external to said first zone and said fourth zone is a zone external to said second zone.

3. The cell culture device according to claim 1, wherein the third zone located entirely below the second zone and entirely above the first zone.

4. The cell culture device according to claim 2 or 3, further comprising flow redistributing elements in the third zone or closed regions in the bottom wall of the second zone for providing a homogenous flow of medium into said second zone.

5. The cell culture device according to claim 2, comprising a series of culture modules ($m_1 \ldots m_n$), each module comprising said first zone, said second zone, said third zone and said fourth zone, and wherein the adjacent modules in said series of culture modules are in medium communication, and said first zone and said fourth zone of each module are in communication with said means for circulating.

6. The cell culture device according to claim 5, wherein the means for circulating is confined in a base module ($m_0$), and wherein said base module ($m_0$) is in medium communication with at least one first medium transfer zone and at least one fourth medium transfer zone, directly or indirectly.

7. The cell culture device according to claim 5, further comprising a head module ($m_t$), said head module ($m_t$) comprising at least the cover.

8. The cell culture device according to claim 1, wherein said at least one fourth zone comprises at least one essentially vertical or inclined flow wall.

9. The cell culture device according to claim 1, wherein said essentially vertical or inclined flow wall comprises a hydrophilic membrane.

10. The cell culture device according to claim 1, further comprising at least one gas inlet orifice and one gas outlet orifice.

11. The cell culture device according to claim 1, wherein the cover of the culture vessel is connected to at least part of said top wall of at least one second zone.

12. The cell culture device according to claim 5, wherein the means for circulating is confined in a base module ($m_0$), wherein said base module ($m_0$) is in medium communication with at least one first medium transfer zone and at least one fourth medium transfer zone, directly or indirectly, wherein each culture module ($m_0 \ldots m_n$) comprises in its top part a first connector and in its bottom part a second connector and wherein said base module ($m_0$) also comprises in a top part ($m_{0b}$) a first complementary connector and said head module ($m_t$) also comprises in its bottom part a second complementary connector for producing a stacking sequence from bottom to top of a base module ($m_0$), at least one culture module ($m_0 \ldots m_n$) and a head module ($m_t$).

13. The device according to claim 12, wherein said connectors for said stacking sequence in a gas- and liquid-tight manner.

14. The device of claim 1, wherein the second zone includes an imperforate side wall.

15. A method of culturing cells in a culture vessel with circulation of a culture medium, comprising the steps of:
introducing the culture medium (M) to means for circulating culture medium and discharging the culture medium (M) therefrom,
transferring the culture medium (M) into and upwardly through a first culture medium transfer zone,
transferring the culture medium (M) into a second cell culture zone,
transferring the culture medium from said first culture medium transfer zone into a third culture medium transfer zone, by overflowing from the first culture medium transfer zone to the third culture medium transfer zone; and
transferring the culture medium from said second cell culture zone into a fourth culture medium transfer zone, by overflowing the culture medium from the second cell culture zone into the fourth culture medium transfer zone, wherein the culture medium flow is generally downwardly in the fourth culture medium transfer zone.

16. The method of culturing cells according to claim 15, also comprising oxygenating of the culture medium during one or more of said transferring steps.

17. The method of culturing cells according to claim 15, wherein the oxygenating is carried out during the transferring of culture medium to the fourth culture medium zone, and wherein said transferring comprises providing a flow of said culture medium (M) along a flow wall.

18. The method of culturing cells according to claim 15, wherein the transferring of culture medium to the fourth culture medium zone comprises flowing the culture medium along a hydrophilic wall.

19. The method of claim 15, wherein the step of overflowing the culture medium from the first zone to the third zone comprises passing the culture medium through an orifice.

20. The method of claim 19, wherein:
the step of transferring the culture medium to the second medium transfer zone comprises moving the culture medium generally upwardly from the first medium transfer zone to the second medium transfer zone, and
the step of transferring the culture medium from the cell culture zone into the third medium transfer zone comprises moving the culture medium generally downwardly from the cell culture zone to the third medium transfer zone.

21. The method of claim 19, wherein the step of transferring the culture medium from the cell culture zone to the third medium transfer zone includes oxygenating the culture medium.

22. A device for culturing cells based on a substantially vertical flow of a culture medium through a fixed bed of media, comprising: a culture vessel provided with a cover, wherein there is situated at least one first zone and at least one second zone, wherein said first zone is a transfer zone for the culture medium essentially containing no cells and said second zone for culturing cells, a pump for circulating the culture medium through the second zone, said second zone comprising a bottom wall, a top wall, and at least one side wall, wherein said top and bottom walls are provided with one or more orifices allowing a transfer of culture medium essentially free from cells, and further comprising at least one third zone and at least one fourth zone, said third and fourth zones comprising medium transfer zones essentially free from cells, wherein said third zone is in medium communication with the first and second zones and wherein said fourth zone is in medium communication with the second zone and with the first zone via the pump for circulating the culture medium, and in that the pump is adapted to circulate the culture medium from bottom to top in said second zone, wherein the culture vessel is arranged such that the culture medium overflows from the first zone to the third zone, and overflows from the second zone to the fourth zone.

23. The device of claim 22, wherein a substantially horizontal wall extends between the first and third zones, said wall including at least one opening for allowing for the overflow between the first and third zones.

24. The device of claim 23, wherein the substantially horizontal wall includes a vertical part adjacent to the opening.

25. The device of claim 24, wherein the vertical part has a first height of up to about 5% of a second height of the third zone.

26. A device for culturing cells based on a substantially vertical flow, comprising:

a culture vessel including at least one first zone and at least one second zone, wherein said first zone is a transfer zone for the culture medium essentially containing no cells and said second zone for culturing cells, said second zone comprising a bottom wall and at least one imperforate side wall, at least said bottom wall being permeable to the culture medium allowing a transfer of culture medium essentially free from cells, and further comprising at least one third zone and at least one fourth zone, said third and fourth zones comprising medium transfer zones essentially free from cells, wherein said third zone is in medium communication with the first and second zones and wherein said fourth zone is in medium communication with the second zone and with the first zone; and means for circulating the culture medium through the bottom wall and into the second zone;

wherein the culture vessel is arranged such that the culture medium overflows from the first zone to the third zone and overflows from the second zone to the fourth zone.

27. The device of claim 26, wherein the bottom wall includes a plurality of orifices.

28. The device of claim 26, further including a fixed bed of media in the second zone.

29. The device of claim 26, further including a plurality of cells.

30. The device of claim 26, wherein the means for circulating comprises a pump positioned in a bottom part of the culture vessel below the bottom wall of the second zone, said bottom part including the first zone.

31. The device of claim 26, further including an elongated solid element extending vertically from the bottom wall to the top wall.

32. A method of culturing cells in a culture vessel, comprising the steps of:

circulating culture medium throughout the culture vessel, including by:
(i) transferring the culture medium generally upwardly through a first medium transfer zone,
(ii) transferring the culture medium from the first medium transfer zone to a second medium transfer zone, including by overflowing the culture medium from the first medium transfer zone to the second medium transfer zone;
(iii) transferring the culture medium upwardly through a cell culture zone from bottom to top; and
(iv) transferring the culture medium from the cell culture zone to a third medium transfer zone, including by overflowing the culture medium from the cell culture zone into the third medium transfer zone.

* * * * *